US006954722B2

(12) United States Patent
Parks et al.

(10) Patent No.: US 6,954,722 B2
(45) Date of Patent: Oct. 11, 2005

(54) METHODS AND SYSTEMS FOR DATA ANALYSIS

(75) Inventors: David R. Parks, San Francisco, CA (US); Wayne A. Moore, San Francisco, CA (US)

(73) Assignee: Leland Stanford Junior University, Palo Alto, CA (US)

( * ) Notice: Subject to any disclaimer, the term of this patent is extended or adjusted under 35 U.S.C. 154(b) by 105 days.

(21) Appl. No.: 10/688,868

(22) Filed: Oct. 17, 2003

(65) Prior Publication Data

US 2004/0143423 A1 Jul. 22, 2004

Related U.S. Application Data

(60) Provisional application No. 60/419,458, filed on Oct. 18, 2002.

(51) Int. Cl.[7] .............................. G06F 15/00; H03F 1/26
(52) U.S. Cl. ...................................................... 702/194
(58) Field of Search ........................... 702/30, 32, 108, 702/124, 127, 189, 190, 194; 382/133–134

(56) References Cited

U.S. PATENT DOCUMENTS 6,592,822 B1 * 7/2003 Chandler .................. 422/82.05
2002/0191824 A1 * 12/2002 Reynolds et al. ........... 382/128

OTHER PUBLICATIONS

Smith (1999) "The Scientist's and Engineer's Guide to Digital Signal Processing." 2nd Ed. Chapter 22 pp. 351–372.
Bagwess and Adams (1993) "Software spectral overlap compensation for any number of flow cytometry parameters." *The New York Academy of Sciences* 20(677): 167–184.

Bickle and Doksum (1981) "An analysis of transformations revisted." *Journal of American Statistical Association* 76: 296–311.
Box and Cox (1964) "Anaylsis of transformations." J. Royal Statist. Soc. Ser B 26: 211–243.
Box and Muller (1958) "A note on the generation of random normal deviates." Ann. Math Stat. 29: 610–611.
Burbidge et al. (1988) "Alternative transformations to handle extreme values of the dependent variable." *Journal of American Statistical Association* (Mar.) 83(401) 123–127.
Guarnieri et al. (1998) "Infrared array photometry of bulge globular clusters." *Astronomy and Astrophysics* 331:70–80.
Holder et al. (2001) "Statistical analysis of high density oligonucleotide arrays: a SAFER approach." In Proceedings of the ASA Annual Meeting, Atlanta, GA, 2001.
Johnson (1949) "Systems of frequency curves generated by methods of translation." *Biometrika* 36: 149–176.
Layton (2001) "Alternative approaches for modeling concave willingness to pay functions in conjoint valuation." Amer. J. Agr. Econ 83(5): 1314–1320.
Loken et al. (1977) "Two–color immunofluorescence using a fluorescense–actvated cell sorter." *Journal of Histochemistry and Cytochemistry* 25: 899–907.

(Continued)

*Primary Examiner*—John Barlow
*Assistant Examiner*—Demetrius Pretlow
(74) *Attorney, Agent, or Firm*—Christopher C. Sappenfield; Quine Intellectual Property Law Group, P.C.

(57) ABSTRACT

The present invention provides methods of analyzing and/or displaying data. In one aspect, the invention provides methods for visualizing or displaying high dynamic range data obtained from flow cytometry analyses. Related systems and computer programs products are also provided.

26 Claims, 30 Drawing Sheets

OTHER PUBLICATIONS

Munson (2001) "A 'Consistency' test for determining the signifance of gene expression changes on replicate samples and two convenient varianc–stabilizing transformations." GeneLogic Workshop of Low Level Analysis fo Affmetrix GeneChip data, *National Institutes of Health*, Nov. 2001.

Ridders (1979) "Transactions on circuits and systems." IEEE vol. CAS–26 (11): 979–980.

Rocke and Durbin (2003) "Approximate variance–stabilizing transformations for gene–expression microarray data." *Bioinformatics* 19(8): 966–972.

Turkey (1964) "On the comparative anatomy of transformations." Ann. of Math Statistics 28: 602–632.

Turkey (1977) "Exploratory data analysis." Addison–Wesley, Reading, MA, Chapter 3; pp. 57–96.

Verity Software House, Inc. (Released commercially Aug. 2003) HyperLog™ MinList 5.0 SP4, http://www.vsh.com/frmain.htm., printed Dec. 23, 2004.

\* cited by examiner

| 120 | Your request has been accepted and is being processed |
| --- | --- |
| 122 | Your results will be ready in approximately ___ minutes. |
| 124 | This request will be charged to account: AccountId (click here to change account information) |
| 126 | The expected charge for this analysis is ___. |
| 128 | Results from this analysis will be transmitted to _____ (click here to change results destination) |

Fig. 27B

METHODS AND SYSTEMS FOR DATA ANALYSIS

CROSS-REFERENCES TO RELATED APPLICATIONS

This application claims the benefit of U.S. Provisional Application No. 60/419,458, filed Oct. 18, 2002, which is incorporated by reference.

STATEMENT AS TO RIGHTS TO INVENTIONS MADE UNDER FEDERALLY SPONSORED RESEARCH AND DEVELOPMENT

This invention was made with Government support under grant No. EB00231 awarded by the National Institutes of Health (Bioengineering grant, Leonard A. Herzenberg, PI). The Government has certain rights to this invention.

COMPUTER PROGRAM LISTING APPENDIX ON COMPACT DISC

Attached herewith are two compact discs (Copy 1 and Copy 2). These discs are identical copies. Each disc includes 19 ASCII files comprising a computer program listing appendix. All material therein is hereby incorporated by reference in this application. The names and indicated sizes of the files on the compact disc are: Parks_et_al_1.txt (4608 bytes), Parks_et_al_2.txt (4608 bytes), Parks_et_al_3.txt (10240 bytes), Parks_et_al_4.txt (11776 bytes), Parks_et_al_5.txt (15872 bytes), Parks_et_al_6.txt (21504 bytes), Parks_et_al_7.txt (22528 bytes), Parks_et_al_8.txt (30208 bytes), Parks_et_al_9.txt (34304 bytes), Parks_et_al_10.txt (42496 bytes), Parks_et_al_11.txt (1536 bytes), Parks_et_al_12.txt (7168 bytes), Parks_et_al_13.txt (8704 bytes), Parks_et_al_14.txt (11264 bytes), Parks_et_al_15.txt (52224 bytes), Parks_et_al_16.txt (1536 bytes), Parks_et_al_17.txt (1536 bytes), Parks_et_al_18.txt (5120 bytes), and Parks_et_al_19.txt (6656 bytes). These files include example source code illustrating specific implementations of specific embodiments of the invention along with explanatory text. These compact discs were created on the filing date indicated above and are in Microsoft® Windows format.

COPYRIGHT NOTIFICATION

Pursuant to 37 C.F.R. 1.71(e), applicants note that a portion of this disclosure contains material that is subject to and for which is claimed copyright protection, such as, but not limited to, source code listings, screen shots, user interfaces, or user instructions, or any other aspects of this submission for which copyright protection is or may be available in any jurisdiction. The copyright owner has no objection to the facsimile reproduction by anyone of the patent document or patent disclosure, as it appears in the Patent and Trademark Office patent file or records. All other rights are reserved, and all other reproduction, distribution, creation of derivative works based on the contents, public display, and public performance of the application or any part thereof are prohibited by applicable copyright law.

BACKGROUND OF THE INVENTION

Flow cytometers are typically used to analyze the properties of single cells. For example, as a single cell suspension interrupts a laser beam of the flow cytometry system at high velocity, it produces a scattering of light from the beam. Data is generally relayed to a computer for interpretation of the results. These systems are typically designed for the enumeration, identification, and sorting of cells possessing selected properties. Fluorescence-activated cell sorting (FACS) is a specific type of flow cytometry, which utilizes fluorescent markers (e.g., fluorochrome-labeled monoclonal antibodies) to label cells in order to detect and sort the cells as part of multi-parameter analyses.

Flow cytometry fluorescence measurement data is currently displayed using either logarithmic or linear scaling. In most applications linear scaling fails to provide appropriate resolution across the typical data range of up to 10,000:1. Logarithmic displays are unable to deal with negative data values and typically introduce biologically artifactual peaks, particularly in data derived through fluorescence compensation. The result is that both the compactness and central tendency of low signal cell populations is severely obscured. Previous attempts to develop improved visualizations (e.g., displaying cytometry data for a human viewer) have not been very successful in that they have involved seriously compromising quantitation and/or introduced their own artifacts into the display (e.g., a simple linear-to-log splice tends to introduce a distinct transition line into the display).

Accordingly, there is a substantial need for improved methods and related systems for analyzing and/or displaying data, e.g., high dynamic range data generated by flow cytometry. These and other attributes of the present invention will be apparent upon complete review of the following.

SUMMARY OF THE INVENTION

The present invention provides, e.g., improved analytical methods and/or displays for flow cytometry data and other (e.g., multidimensional) data types to promote correct and accurate interpretation of the information contained therein. Related systems and computer program products are also described herein.

In one aspect, the invention relates to a method of analyzing data using a computer. The method includes receiving raw data (e.g., high dynamic range data or the like) at the computer, and scaling the raw data using at least one scaling function that provides substantially linear transformations for data values proximal to zero and substantially logarithmic transformations for other data values to generate scaled data. In certain embodiments, the raw data is derived through fluorescence compensation. The method also includes using the scaled data to identify portions of the raw data of interest. This aspect of the invention is further illustrated in FIG. 1.

In another aspect, the present invention relates to a method of analyzing flow cytometry data (e.g., high dynamic range data or the like) using a computer. The method includes receiving raw data at the computer, which raw data comprises data from a plurality of light detectors of a flow cytometry system (e.g., a fluorescence-activated cell sorting flow cytometry system or the like). The raw data is typically derived through fluorescence compensation. The method also includes scaling the raw data in the computer using at least one scaling function that provides substantially linear transformations for data values proximal to zero and substantially logarithmic transformations for other data values to generate scaled data. Typically, the scaling comprises specifying at least one preliminary parameter such that other variables are constrained by one or more criteria of the scaling function to define at least one single variable transformation (e.g., a family of related transformations, etc.). In addition, the method further includes using the scaled data to identify portions of the raw data of interest. In preferred embodiments, a transition from linear to logarithmic scaling in the scaled data is substantially smooth (i.e., not including a distinct transition line).

Various other criteria also typically describe the scaling function of the present invention. In preferred embodiments, for example, the scaling function transforms negative raw data values. Typically, the second derivative of the scaling function is zero for a corresponding raw data value of zero. The scaling function is generally substantially symmetrical proximal to a raw data value of zero. In addition, the scaling function typically comprises one or more optimization functions for viewing different raw data sets.

In certain embodiments of the method, using comprises displaying the scaled data for a human viewer. For example, the scaled data is typically displayed on a coordinate grid and the scaling function primarily depends on data in a single data dimension to assure that the coordinate grid is substantially rectilinear. Display values generally increase in size more than corresponding display variables in linear regions of the scaled data as a family-generating variable is adjusted to increase a range of linearity. The scaling function typically includes at least one generalized hyperbolic sine function. In some embodiments, the generalized hyperbolic sine function is in a form of $V=Z(10^{n/m}-1-G^2(10^{-n/mG}-1))$, where V is a data value to be displayed at channel position n in a plot of said scaled data, m is the asymptotic channels per decade, and G is linearization strength. In certain embodiments, the generalized hyperbolic sine function is a form of $V=a\ (e^x-p^2e^{-px}+p^2-1)$, where V is a data value to be plotted at display position x in a plot, a is a scaling factor, and p is linearization strength. Optionally, the generalized hyperbolic sine function is a form of $S(x;\ a,\ b,\ c,\ d, So)=ae^{bx}-ce^{-dx}-So$, for positive x and for negative x, a reflection of the positive x in a form of $Sref(x;\ a,\ b,\ c,\ d, So)=(x/absx)\ S(absx;\ a,\ b,\ c,\ d,\ So)$, where absx is the absolute value of variable x. In some embodiments, using comprises inputting said scaled data into at least one data analysis algorithm (e.g., automated data analysis software, such as cluster analysis software and the like) to identify the portions of the raw data of interest.

In another aspect, the present invention relates to a computer program product that includes a computer readable medium having one or more logic instructions for receiving raw data in a computer, which raw data comprises data from a plurality of light detectors of a flow cytometry system, and scaling the raw data using at least one scaling function that provides substantially linear transformations for data values proximal to zero and substantially logarithmic transformations for other data values to generate scaled data. The computer readable medium typically includes one or more of, e.g., a CD-ROM, a floppy disk, a tape, a flash memory device or component, a system memory device or component, a hard drive, a data signal embodied in a carrier wave, or the like.

In still another aspect, the invention provides a system for analyzing flow cytometry data. The system includes (a) at least one flow cytometer, and (b) at least one computer operably connected to the flow cytometer, which computer has system software. The system software includes one or more logic instructions for receiving raw data in the computer, which raw data comprises data from a plurality of light detectors of a flow cytometry system, and scaling the raw data using at least one scaling function that provides substantially linear transformations for data values proximal to zero and substantially logarithmic transformations for other data values to generate scaled data. In preferred embodiments, the system software further includes one or more logic instructions for displaying the scaled data for a human viewer. In some embodiments, the system software further comprises one or more logic instructions for analyzing the scaled data to identify portions of the raw data of interest (e.g., automated data analysis software, such as cluster analysis software or the like).

In some embodiments, analysis according to the invention can be accessed using an information processing system and/or over a communications network. According to specific embodiments of the invention, a client system is provided with a set of interfaces that allow a user to indicate one or more analyses and/or analysis parameters and that may direct a user to input the necessary initial data or option selections. The client system displays information that identifies analysis available and displays an indication of an action that a user is to perform to request an analysis. In response to a user input, the client system sends to a server system the necessary information. The server system uses the request data, and optionally one or more sets of server data, to perform the requested analysis. Subsequently, results data are transmitted to the client system. In specific embodiments, such analysis can be provided over the Internet, optionally using Internet media protocols and formats, such as HTTP, RTTP, XML, HTML, dHTML, VRML, as well as image, audio, or video formats, etc. However, using the teachings provided herein, it will be understood by those of skill in the art that the methods and apparatus of the present invention could be advantageously used in other related situations where users access content over a communication channel, such as modem access systems, institution network systems, wireless systems, etc. Thus, the present invention is involved with a number of unique methods and/or systems that can be used together or independently to provide analysis related to biologic or other data. In specific embodiments, the present invention can be understood as involving new business methods related to providing such analysis.

The invention and various specific aspects and embodiments will be better understood with reference to the following drawings, appendix, and detailed descriptions. In some of the drawings and detailed descriptions below, the present invention is described in terms of the important independent embodiment of a system operating on a digital data network. This should not be taken to limit the invention, which, using the teachings provided herein, can be applied to other situations, such as cable television networks, wireless networks, etc. For purposes of clarity, this discussion refers to devices, methods, and concepts in terms of specific examples, e.g., flow cytometry. However, the invention and aspects thereof have applications to a variety of types of devices and systems. It is therefore intended that the invention not be limited except as provided in the attached claims.

It is well known in the art that logic systems and methods such as described herein can include a variety of different components and different functions in a modular fashion. Different embodiments of the invention can include different mixtures of elements and functions and may group various functions as parts of various elements. For purposes of clarity, the invention is described in terms of systems and/or methods that include many different innovative components and innovative combinations of innovative components and known components. No inference should be taken to limit the invention to combinations containing all of the innovative components listed in any illustrative embodiment in this specification. The functional aspects of the invention that are implemented on a computer, as will be understood from the teachings herein, may be implemented or accomplished using any appropriate implementation environment or programming language, such as C, C++, Cobol, Pascal, Fortran, Java, Java-script, PLI, LISP, HTML, XML, dHTML, assembly or machine code programming, etc. All references, publications, patents, and patent applications cited herein are hereby incorporated by reference in their entirety for all purposes. All documents, data, and other written or otherwise available material described or referred to herein, are incorporated by reference.

DETAILED DISCUSSION OF THE INVENTION

Introduction

Figure 1:
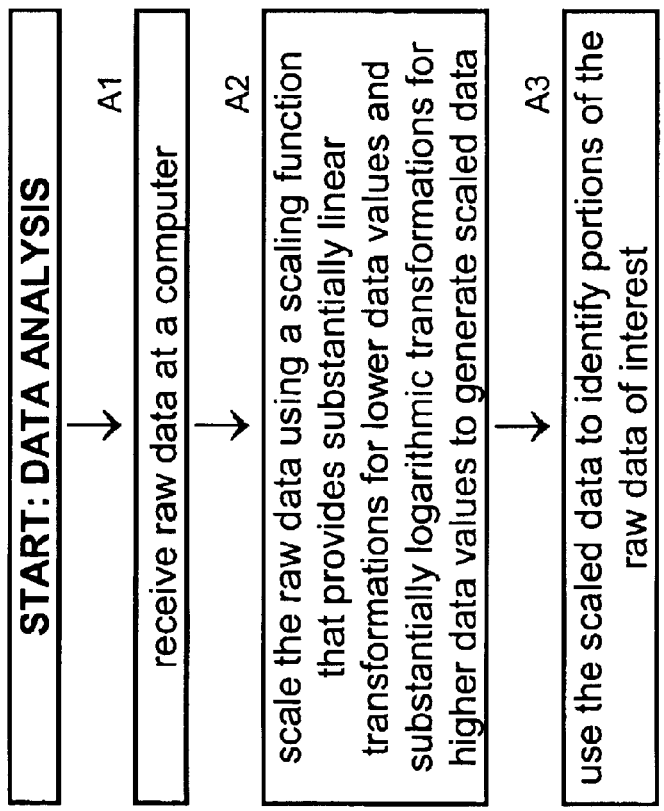
FIG. 1 is a flow chart illustrating a method of analyzing data according to specific embodiments of the invention.

Before describing the present invention in detail, it is to be understood that this invention is not limited to particular methods, devices, or systems, which can, of course, vary. It is also to be understood that the terminology used herein is for the purpose of describing particular embodiments only, and is not intended to be limiting. In addition, unless defined otherwise, all technical and scientific terms used herein have the same meaning as commonly understood by one of ordinary skill in the art to which the invention pertains. Furthermore, it is to be understood that although the methods, systems, and other aspects of the invention are described herein, for purposes of clarity of illustration, with particular reference to flow cytometry, such reference is not intended to be limiting.

When flow cytometry data is properly compensated, it is common that a large number of cells are displayed crowded or poorly resolved proximal to a display axis. The cells typically become piled up in the first channel (against the axis) because the fluorescence parameters are displayed on a log scale where it is not possible to display "zero" or negative values. The spreading of a population into negative compensated data values is generally the result of statistical error in measurement that is inherent in the data collected on flow cytometers. Even though the measurement error is the same in uncompensated samples, the variation becomes obvious when a compensated population has a low mean and therefore appears in the low regions of the log scale. This is because log scales expand the view of data in the lower regions (first decade) and compress the view of data in the upper regions (fourth decade). The display transformations of the present invention provide data on an altered scale, e.g., that has a zero and a negative region. The data values are the same as before the transformation, because only the display is changed as described herein. For example, the display transformations of the present invention typically allow negative populations to be viewed as substantially symmetrical clusters instead of being poorly resolved near the display axis. Moreover, linear data can also be transformed as described herein to provide a more interpretable view instead of the "picket fences" that are frequently observed at the low end of 5+ decade log scales.

Regardless of the methods used to visualize the data and/or to delineate related groups of cells or other data events, the computations of statistics typically use the underlying best estimate data. This is not currently the case in some situations using pre-existing commercial flow cytometry software. In particular, very low and negative values may be truncated and computed as bottom of display scale values.

In evaluating possible scaling functions for displaying or visualizing data a set of criteria has been devised for the behavior of the scaling function and various parametrizations have been explored in order to fulfill the criteria. In particular, a set of criteria for a desirable transformation include, as follows:

1. The data scaling itself utilizes only single dimension data, and 2-D plots of such data will have straight, orthogonal grids of signal levels. Stated otherwise, the display function should depend only on data in a single data dimension, assuring that the coordinate grid is rectilinear. This assures that each data event is displayed at a position corresponding to its best estimate values, including negative values. (Note, that although this may seem like an obvious criterion, some pre-existing displays used in flow cytometry violate it due to electronic anomalies, and certain proposals have been made to devise transformations that will not plot as a rectilinear grid.).
2. The function becomes asymptotically logarithmic for high values of the display variable.
3. The function becomes linear proximal or near zero and extends to display negative values. Maximizing the near-linear range and making it symmetrical around zero signal level indicates that the second derivative of the function is zero at a zero data value.
4. The display formula supports a family of functions, which can be optimized for viewing different data sets.
5. The transition from linear to logarithmic behavior is substantially smooth, that is, does not have a distinct transition.
6. The reasonably linear zone grows in display value faster than in the display variable as the family variable is adjusted. For example, if the linearized zone were doubled in width in the plot it might cover four times the data range.
7. The function is substantially symmetrical around zero data value.

In some embodiments, a method for fulfilling these criteria and producing improved data displays is produced using generalized forms of the hyperbolic sine function (sinh). This array of functions, their mathematical properties, specifications for using them to construct functions meeting the criteria stated above, and computational suggestions are described further below.

Once certain basic conditions, e.g., for the asymptotic scaling have been set, sufficient flexibililty is provided by having only one remaining variable to specify different versions of the family of display functions. Further, once preliminary parameters have been specified, the remaining variables are constrained by the criteria described above to define an effectively single variable transformation (i.e., a family of related transformations) which is suitable for automatic adjustment of the model parameter based on the set of data to be displayed in order to optimize, e.g., display or visualization.

The methods and other aspects of the present invention provide various advantages relative to many pre-existing approaches. To illustrate, the data scaling is specified by a mathematically well-defined function that can be readily computed. Also, variation in one parameter of the function creates a family of transformations whose members can be selected to optimize display of particular data sets. In addition, the linear to logarithmic transition is very smooth, minimizing the likelihood that display artifacts will be created. Further, the method retains a rectilinear display grid (lines of equal signal level are straight and horizontal or vertical). Moreover, for flow cytometry measurement data, the negative data values are produced as a result of computations in which population means should not be negative but the individual data points vary due to noise and statistical variations in the original data. In such a case, the data points with negative values should not form new populations or show structure beyond falloff of the statistical distribution with more negative values. This property is useful in testing for errors in the data or data computations or for improper choice of the display variable.

Other functional forms or ad hoc transformations that meet the criteria described above to provide displays that are improved relative to pre-existing displays are also contemplated.

Biexponential Functions

Mathematical Background

Consider the functions $$s(x;a,b,c,d)=ae^{bx}-ce^{-dx}$$

$$c(x;a,b,c,d)=ae^{bx}+ce^{-dx}$$

where a, b, c, d>0. For example, $$s(x;1/2,1,1/2,1)=\sinh x$$

$$c(x;1/2,1,1/2,1)=\cosh x.$$

Notice that they are closed under arbitrary linear transformations of the argument, i.e., $$s(xy+z;a,b,c,d)=ae^{b(xy+z)}-ce^{-d(xy+z)}=s(x;ae^{bz},by,ce^{-dz},dy)$$

$$c(xy+z;a,b,c,d)=ae^{b(xy+z)}+ce^{-d(xy+z)}=c(x;ae^{bz},by,ce^{-dz},dy)$$

They have derivatives $$\frac{d}{dx}s(x;a,b,c,d) = abe^{bx}+cde^{-dx}=c(x;ab,b,cd,d)$$

$$\frac{d}{dx}c(x;a,b,c,d) = abe^{bx}-cde^{-dx}=s(x;ab,b,cd,d)$$

and the sinh like functions have roots $$\frac{d^{2n}}{dx^{2n}}s(x_n;a,b,c,d)=s(x_n;ab^{2n},b,cd^{2n},d)=0$$

for $$x_n=\frac{\ln c-\ln a}{b+d}+2n\frac{\ln d-\ln b}{b+d}$$

Usually b>d is desired so that the roots eventually become negative. We can take $$w = -2\frac{\ln d - \ln b}{b + d}$$

as a dimensionless parameter and then $$x_n = x_0 - nw.$$

By definition, $x_0$ is the point where the function s crosses zero and thus the point where the positive and negative exponential terms are equal. The point where the second derivative vanishes is $x_1$ and at that point the first derivative reaches its global minimum. Also, the functions are most nearly linear in the neighborhood of $x_1$.

To apply these ideas to data visualization the $\sinh^{-1}$ like functions are exploited, which functions are essentially logarithmic for large arguments while also being nearly linear over a finite interval. Take x as the display coordinate and y as the data coordinate, then define a slightly more general set, the biexponential functions $$B = \{\beta(x) = ae^{bx} - ce^{-dx} + f\}$$

and their inverses $$\Lambda = \{\lambda(y) \text{ where } \lambda^{-1}(x) \in B\}.$$

Since the functions β are continuous and monotonic the inverse functions λ are always well defined globally. Usually we will want a, b, c, d>0 but if we take the closure $\overline{B}$, i.e., weak inequality, we see that log y (y+c') $\in \overline{\Lambda}$. Therefore, the ordinary logarithm that is commonly used for data visualization and also the transform log(y+c), which has been proposed, are boundary points of B. Note that the inverse map $^B \leftrightarrow ^\Lambda$ is bijective but $^{\overline{\Lambda}} \to ^{\overline{B}}$ is surjective.

A data visualization transform must not depend on the location or scaling of the resulting graphic on the page or display. B is closed under such transformations. Conversely, for any $\lambda(y) \in \Lambda$ defined on an arbitrary display interval $[x_{min}, x_{max}]$ one can find values of the parameters that bring this data transform onto the interval [0, 1]. Therefore, without loss of generality, one may assume that this has been done once and for all. In these coordinates, the parameters depend only on the properties of the data transform and those properties are manifestly invariant under any linear viewing transform.

As stated there are five degrees of freedom in B. For flow cytometry one typically wants the linear region to be centered on data value y=0 so we require that $\beta(x_1)=0$ and $\beta''(x_1)=0$ by definition, fixing two of them. Therefore $\lambda(0)=x_1$. $\beta'(x)$ is at its minimum while $\lambda'(y)$ reaches a maximum, i.e., the display space per data unit is greatest in the neighborhood of zero. We call the remaining subset the "logical" functions. Note that $\sinh^{-1} \in \Lambda'$ but $\log \notin \Lambda'$.

We have seen that the choice of w fixes one degree of freedom. We have found it useful to keep $y_{max}$ the maximum data value fixed and located at the upper end of the display scale, i.e., $y_{max}=\beta(1)$. Finally, we define the dilation at a point $D(y)=\lambda'(y)/\lambda'(y_{max})$, which measures the relative amount of display space given to a unit of data near that value. For example, for the logarithm $D(y) \propto 1/y$ everywhere, which is an elaborate way of stating the well known scale invariance of logarithmic plots. The virtue of this approach is that in the case of the logicle functions it remains bounded and is well defined at the origin. In fact, the function is now fixed by the choice of $D_0 = D(0) = y'_{max}/y'_{min}$, the dilation in the neighborhood of zero. If we take a logarithmic scale with $D_{log} = D(y_{min}) = y_{max}/y_{min}$, then a logicle scale with $x_1 = 0$ that matches the log scale for large values will have $$D_0 < \frac{1}{1 + \frac{b}{d}} D_{log}$$

and for $D_{log} > 100$ $$D_0 \approx \frac{1}{1 + \frac{b}{d}} D_{log}$$

or when $w$ is moderate even $D_{log} > 10$. We see that a logicle scale will have at most half the dilation of the corresponding logarithmic scale. Increasing $w$ will decrease $D_0$ as will increasing $x_1$ as long as we keep $y_{max}$ fixed.

Thus the parameters $x_1$, $D_0$ and $w$ characterize the visually important features of the logicle transforms. Note that both the parameters and the logicle condition itself are independent of a change in data units or "gauge" transformation. Therefore all dimensional information is contained in $y_{max}$. The logicle functions satisfy all the mathematical requirements for data visualization.

Choosing the Parameters from Data

Start with a distribution that is unimodal and crosses zero in some logicle scale. Increasing the dilation $D_0$ visually "splits" this distribution noticeably, which is undesirable. Generally we wish to decrease $D_0$, i.e., to reduce the display space given to relatively small absolute values. If the distribution is rescaled, i.e., the data values are all multiplied by some constant k, then if we choose $D_0 \propto 1/k$, features of this distribution remain fixed with respect to one another in display space. However, this is strictly true only at zero and in practice even this prescription falls behind for large multipliers. If we keep large data values unchanged and $w=0$ then increasing $x_1$ decreases $D_0$. This transformation is very similar in behavior to the European companding function but is continuous in the higher derivatives. Increasing $w$ also decreases $D_0$ but not as quickly as increasing $x_1$ so the distribution will broaden somewhat in the display. As discussed below, we have found that utilizing these effects equally is an effective strategy and this broadening gives the user information on the strength of the effect.

We will estimate the scale k by measuring some feature $Y_{ref}$ from the distribution. Since we expect there may be more events in the tail than in a normal distribution, we take as the scale the fifth percentile of the negative data values. This seems to balance sensitivity to extremal events with reasonable sampling stability. We estimate $k = y_{ref}/y_{min}$ (probably this should be $k = 2y_{ref}/y_{min}$).

Then we want to choose $w$, $x_1$ and $D_0$ appropriately. We have found it useful to impose an additional constraint, which is reasonable for flow cytometry but is not required and might not be optimal for all applications. Since the width $w$ of the nearly linear region will be set by the most negative values observed we will always choose $x_2=0$, i.e., this point will be the lowest visible point on the scale. This implies that $x_1 = w$ in display coordinates and that $x_1 \in [0,1]$ so that this point will be "on scale", i.e., visible to the user. Note that in the original implementation we don't use the transfer function directly in this region but rather its reflection in $x_1$ for symmetry. If the $x_2=0$ condition is always imposed, the difference is most likely negligible visually but if more negative values are included in the display, it will rapidly become important.

We have used two strategies for choosing the parameters. The preferred method is to fix $$D_{log} = 10^{4.5}$$

so that large data values are essentially fixed, which is desirable. Then we take $$w = \frac{\ln \sqrt{k}}{\ln D_{log}}$$

and that gives $$D_0 \approx \frac{1}{1 + \frac{b}{d}} \frac{D_{log}}{\sqrt{k}}$$

consequently some distortion of the distribution at small absolute values, i.e., the nearly linear region occurs. If zero falls on the shoulder of the distribution, this can produce a spurious peak but otherwise, it should be visually innocuous. We arrived at the value $10^{4.5}$ empirically but in retrospect it appears the value $D_{log} = 2 \times 10^4$ would be an appropriate choice for a "four decade" logicle scale.

We originally used $$D_{log} = k10^{4.5}$$

This choice of $D_{log}$ keeps only $y_{max}$ fixed, i.e., not large data values in general. Choosing $$w = \frac{\ln k}{\ln D_{log}}$$

gives $$D_0 \approx \frac{1}{1 + \frac{b}{d}} 10^{4.5}$$

Other than a simple rescaling, this would keep the nearly linear region fixed in itself. However, the need for a higher value of $w$ means increasing distortion in the logarithmic region and the scale is accurately logarithmic over a smaller range. For a given range of linearization, the previous method allows some distortion of the linear region but produces much less distortion of the logarithmic region.

The results will be suspect if $w$ is so large that $D_0 < 10$, i.e., when the linear region reaches the upper most decade.

Computing Logicle Transforms

We start with a sample $Y_i$ for i=1, . . . , n of data values. For flow cytometry these will be a linear combination of measured fluorescence emissions that is our best estimator of the amount of dye associated with a cell. We desire to convert this data to a chosen logicle scale so that $X_i = \lambda(Y_i)$. Using Newton's method we could solve $\beta(X_i) = Y_i$ with quadratic convergence at the cost of two exponential function evaluations per iteration. While binary search gives only linear convergence, it requires only two square root evaluations per iteration, which will be faster at lower resolutions. For data visualization we will usually use $X_i$ to choose a pixel coordinate or histogram bin and thus we are limited to a total number of distinct values m within an order of magnitude of $10^3$. If n>m then it will be fastest to tabulate the values of the function $\beta$ in memory and if $n >> m$ as is typical of flow cytometry it will be much faster.

For convenience, we will always work in the standard display coordinate system [0,1]. Therefore the practical problem is to find numerical values for the parameters a, b, c, d, f and then to compute $\beta[j] = \beta(j/m)$ for n=0, . . . , m. We have chosen $D_{log}$ by convention and thus $b = \ln D_{log}$. Using a modified Newton's method (Numerical Recipes) we then solve $$w = 2 \frac{\ln b - \ln d}{b + d}$$

for d, where $w$ is chosen as described above. We then use the condition $x_2 = 0$ to compute $$\frac{c}{a} = e^{2w(b+d)}$$

the condition $\lambda(0) = x_1$ to compute $$\frac{-f}{a} = e^{bw} - \frac{c}{a} e^{-dw}$$

and finally the condition $\lambda(y_{max}) = 1$ $$\frac{y_{max}}{a} = e^b - \frac{c}{a} e^{-d} + \frac{f}{a}$$

and the value of $y_{max}$ to compute a. From these constants and two exponential function values we can then compute $\beta[j]$. When m is a power of 2 the recurrence $$e^{\frac{x+y}{2}} = \sqrt{e^x e^y}$$

provides an accurate and efficient method of computing the required exponentials.

Visualization of FACS Data: Logicle Axes

The pre-existing contour and dot plots that are used by most laboratories have standard four-decade logarithmic axes that provide a wide dynamic range for display of FACS data. However, the absence of a zero point and negative values on these logarithmic axes introduces major problems, particularly for visualizing cells with little or no associated fluorescence. This interferes with visualizing compensated data, since the subtraction of spectral overlap during compensation is designed to return cells with no associated fluorochrome to background values. Statistical variation in the number of photoelectrons detected typically results in "negative" cell populations with more spread in compensated data values than would be observed for the same set of cells completely unstained. In such circumstances some cells commonly receive negative data values that are simply part of the overall distribution for the population. If compensation values are appropriately set, compensated data values for a cell population that is negative for a particular dye can be expected to distribute symmetrically around a low value representing the autofluorescence of the cells in that dye dimension. Logarithmic displays, however, cannot accommodate zero or negative values. This situation can be understood as follows: on a logarithmic scale, all values below the lowest decade must either be discarded (not acceptable) or "piled up" at the lowest point on the scale. The pile-up obscures the true center of the compensated distribution. Furthermore, it often breaks the distribution artificially into what appears to be two subsets, one centered on the pile-up (the lowest point on the scale) and the other centered higher than the true center of the compensated population (see FITC-positive cells in FIG. 2, panel B). This data display artifact often results either in misinterpretation of the higher "population" as a weakly positive subset or in serious over-compensation of the entire data set due to attempting to force this "population" down to the axis.

The Logicle data display, described herein, addresses these problems by enabling visualization of FACS data on mathematically defined axes that are asymptotically linear in the region just above and below zero and asymptotically logarithmic at higher (positive and negative) values. Thus, compensated values that fall either above or below zero can be correctly displayed. Note that logicle visualization does not change the data. It merely allows lower data values to be properly represented and allows peaks in the region around zero to be located in their proper position.

Figure 2:
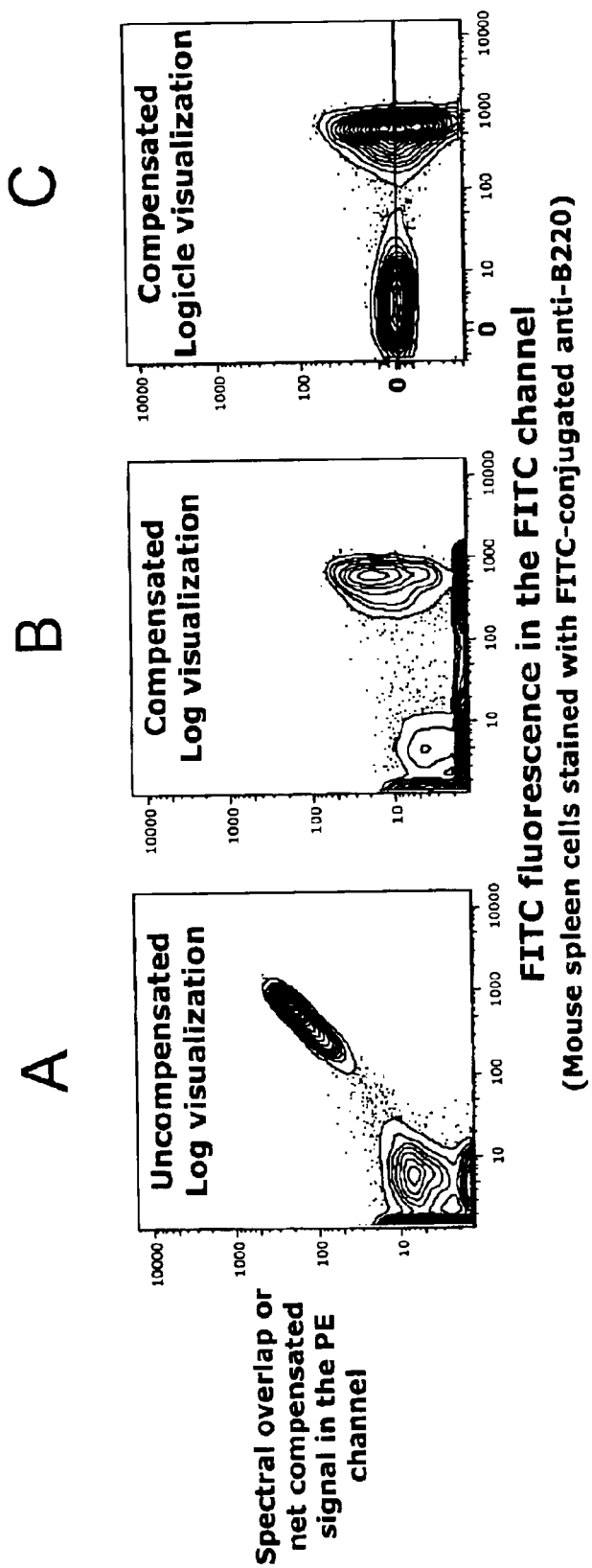
FIGS. 2A–C show FACS data for mouse spleen cells stained with FITC-conjugated anti-B220.

FIG. 2 illustrates how the Logicle display makes it easy to confirm the accuracy of fluorescence compensation. This figure shows data for a cell sample stained only with an FITC reagent. This stain divides the cell sample into two subsets. One subset is not stained by the FITC reagent while the other has a high FITC signal with significant spectral overlap detected on the PE channel (FIG. 2, panel A). In a properly compensated sample involving only PE and FITC staining, the spectral overlap will be subtracted from the fluorescence collected on the PE channel and the signals for all populations on the PE channel will be distributed symmetrically around the autofluorescence value for the cells in the sample (FIG. 2, panel C). When multiple fluorochromes are involved, the compensation calculations are more complex, but the end result is the same: the spectral overlaps are corrected and the distribution representing cells that do not bind the fluorochrome detected in a given channel wind up in a peak centered on their mean autofluorescence value.

Figure 3:
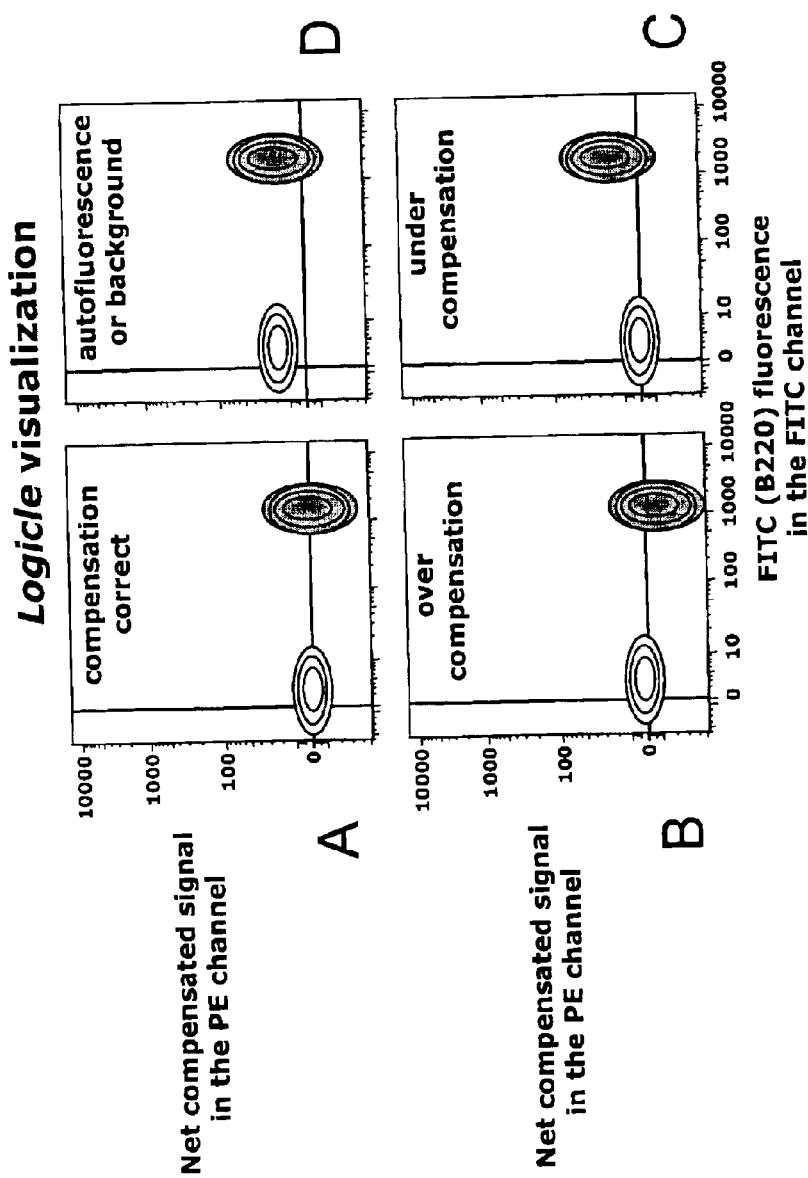
FIGS. 3A–D show expected logical plots for cells that are properly compensated, overcompensated, undercompensated or autofluorescent.
Figure 4:
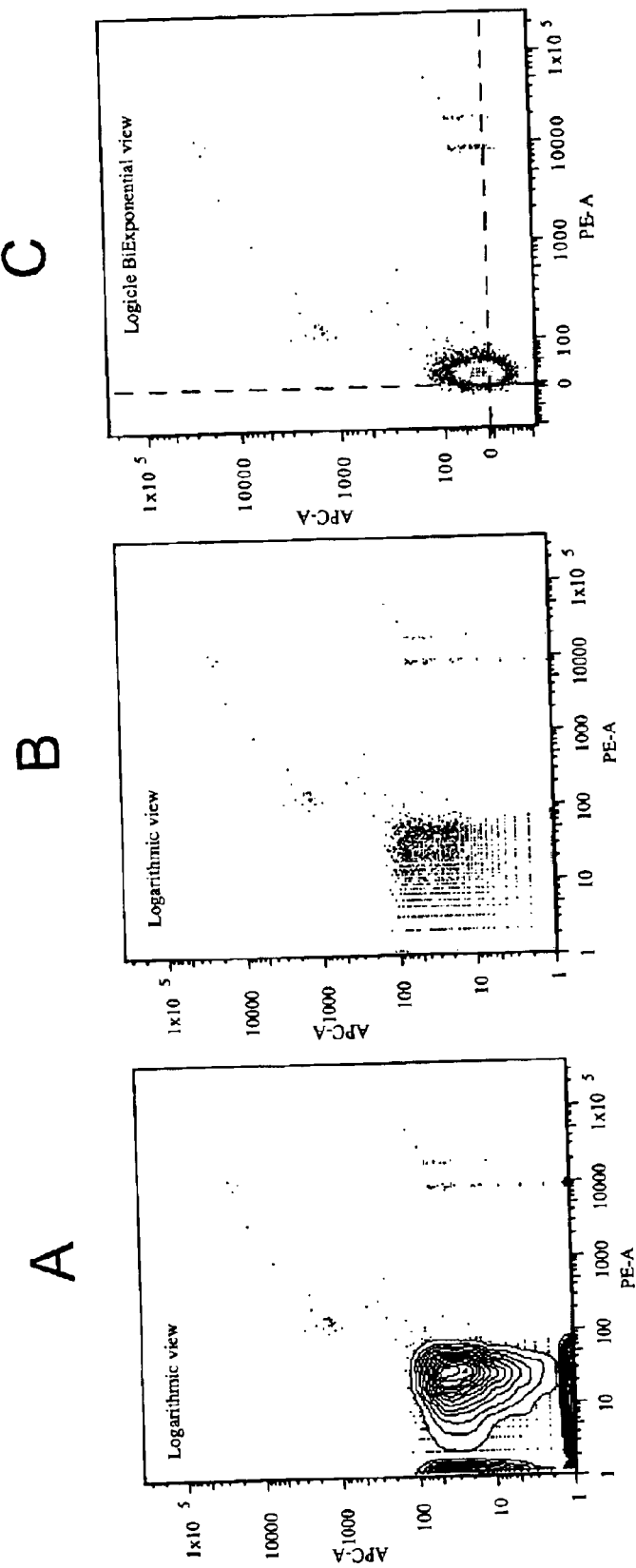
FIGS. 4A–C show data plots for wide range linear data.
Figure 5:
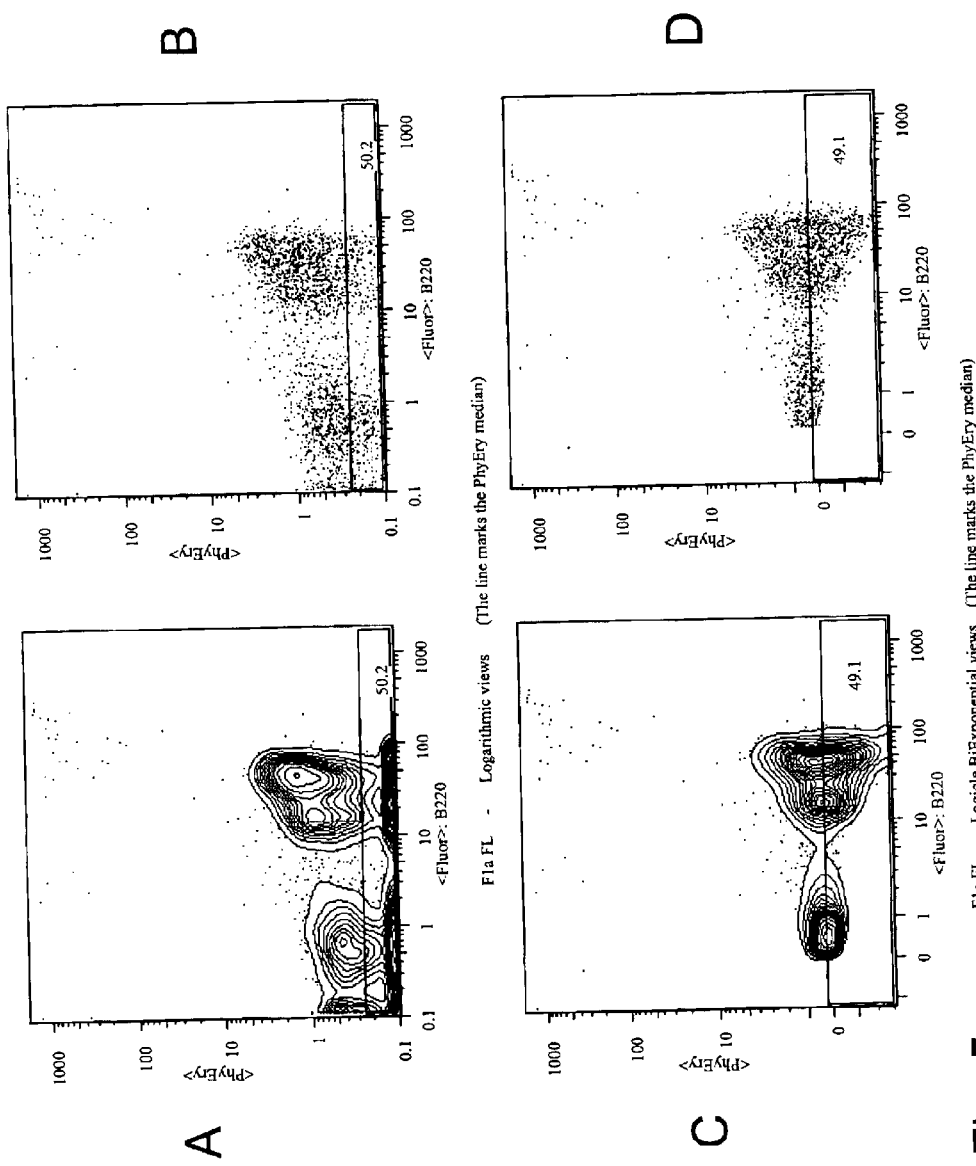
FIGS. 5A–D show log and logical data displays of a compensated single stain control.
Figure 6:
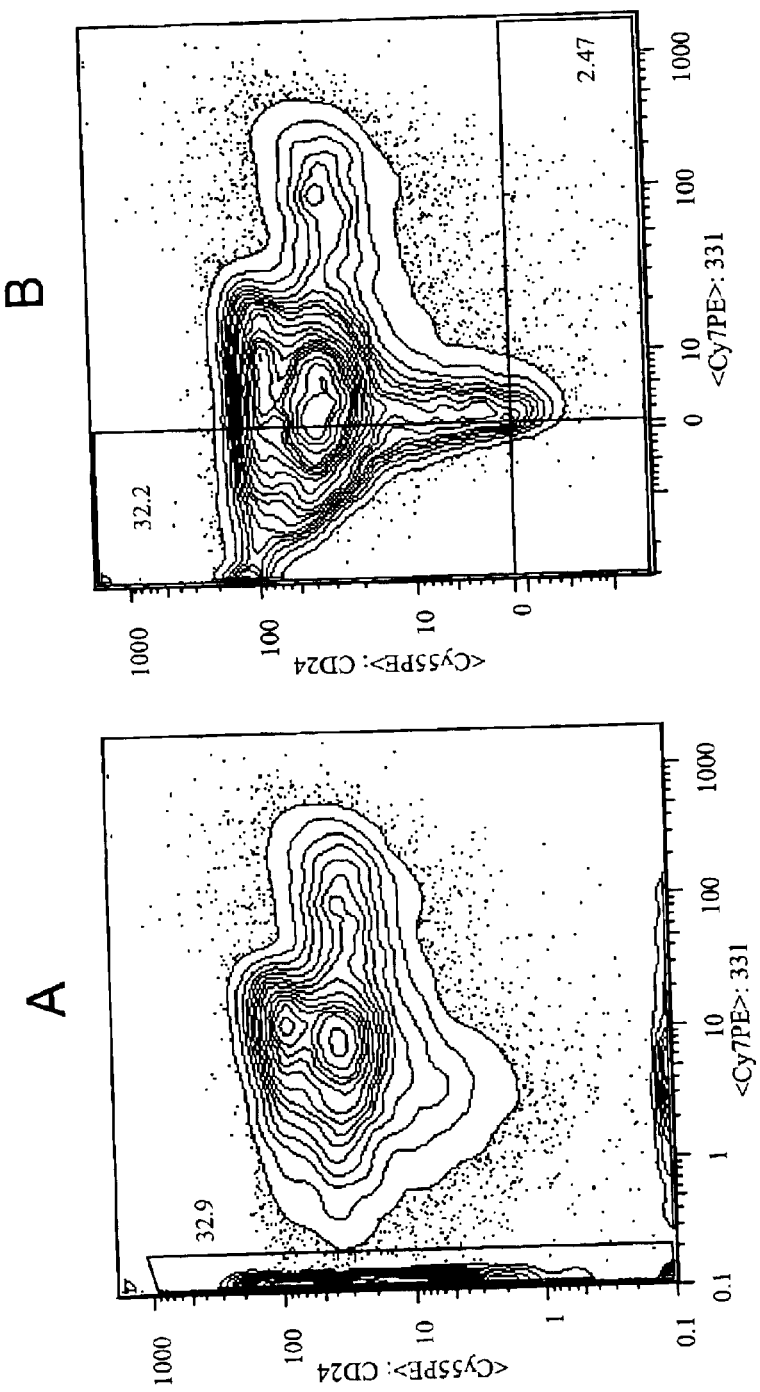
FIGS. 6A and B show log and logical displays of data with high variance and many negatives.

The diagram in FIG. 3 shows the expected logicle plots for cells that are properly compensated (panel A), overcompensated (panel B), undercompensated (panel C), or autofluorescent (panel D). Note that overcompensation drives the peak for the FITC-positive population below the mean autofluorescence in the PE channel while undercompensation fails to bring this population to equivalence with the FITC-negative population. For cells that are equally autofluorescent in the PE channel, both the FITC-positive and the FITC-negative cells will be distributed symmetrically around the mean PE channel autofluorescence value.

Further Description of the Logicle Methods

The display methods described herein reliably customize the display parameters to particular data. A working implementation is available on the world wide web at flowjo.com.

The methods described herein overcome many of the problems with log displays of data using matrix computed compensation. It has turned out that analog compensation as normally implemented not only tends to overcompensation and distorts data, but it also makes the overcompensated single stain control populations look much more compact than is possible from the statistical quality of the actual data. Thus, we have to explain both the comforting distortion of the analog compensated data and deal with visualizing the correct but more spread out computed compensation results.

As described herein, the Logicle scaling is a particular generalization of the hyperbolic sine function ($\sinh(x)=(e^x-e^{-x})/2$). The hyperbolic sine is a good point of departure because it is close to linear around zero (second derivative equals 0 at 0 data value), allows negative values to be plotted, becomes essentially exponential for high data values and makes a very smooth transition between the linear and exponential regions. When this is used as a plotting function, data in the near linear zone gives a near linear display while data in the near exponential zone gives an effectively log display (a pure log display would be obtained by taking just $e^x$ with scaling adjustments).

The hyperbolic sine function in itself, however, does not provide sufficient adjustability to meet the needs for plotting compensated fluorescence data. Therefore, a generalized biexponential functions which add separate coefficients for each of the two exponential terms and for their exponents is typically utilized. The Logicle function constrains or limits the general biexponential in ways that are appropriate for plotting cytometric data. The biexponential coefficients vary but their relationships are linked so that the effective adjustments are in the range and steepness of the linear zone while the most linear zone stays centered at zero, etc. In this way the Logicle function has more adjustable variables than the hyperbolic sine but not as many as a fully general biexponential.

The way Logicle displays are implemented in, e.g., FlowJo 4.3 (available on the world wide web at flowjo.com) is to examine the compensated data set used in defining the transformation to see how much range of linearization is needed in each compensated dye dimension. The specific method is to find the 5th percentile data value among the negative data in each dye dimension. This value is used to select the adjustable parameters in the Logicle function so that the resulting display will have just enough linearity to suppress the "log display artifact" of peaks not being at the actual center of data distributions and will show enough negative data range to bring almost everything on scale.

Figure 7:
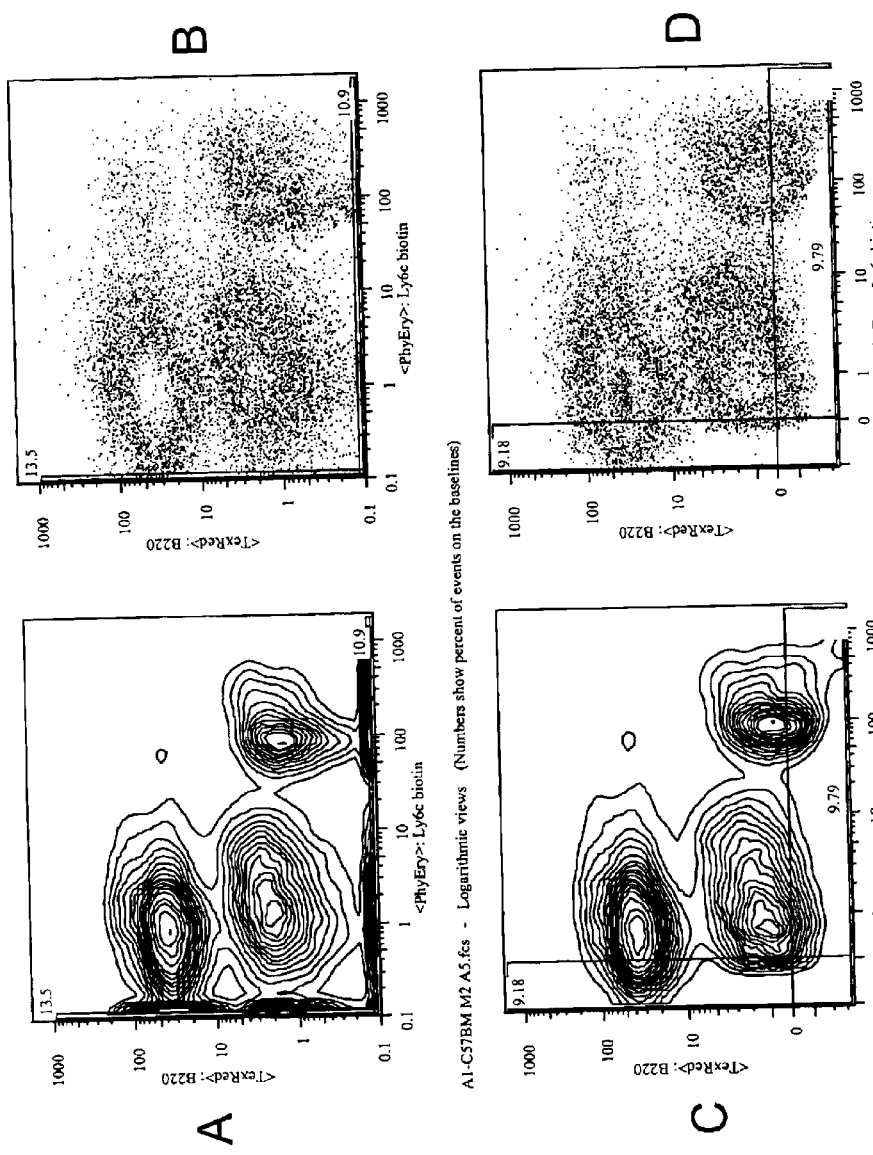
FIGS. 7A–D show log and logical displays of data with moderate numbers of negatives.
Figure 8:
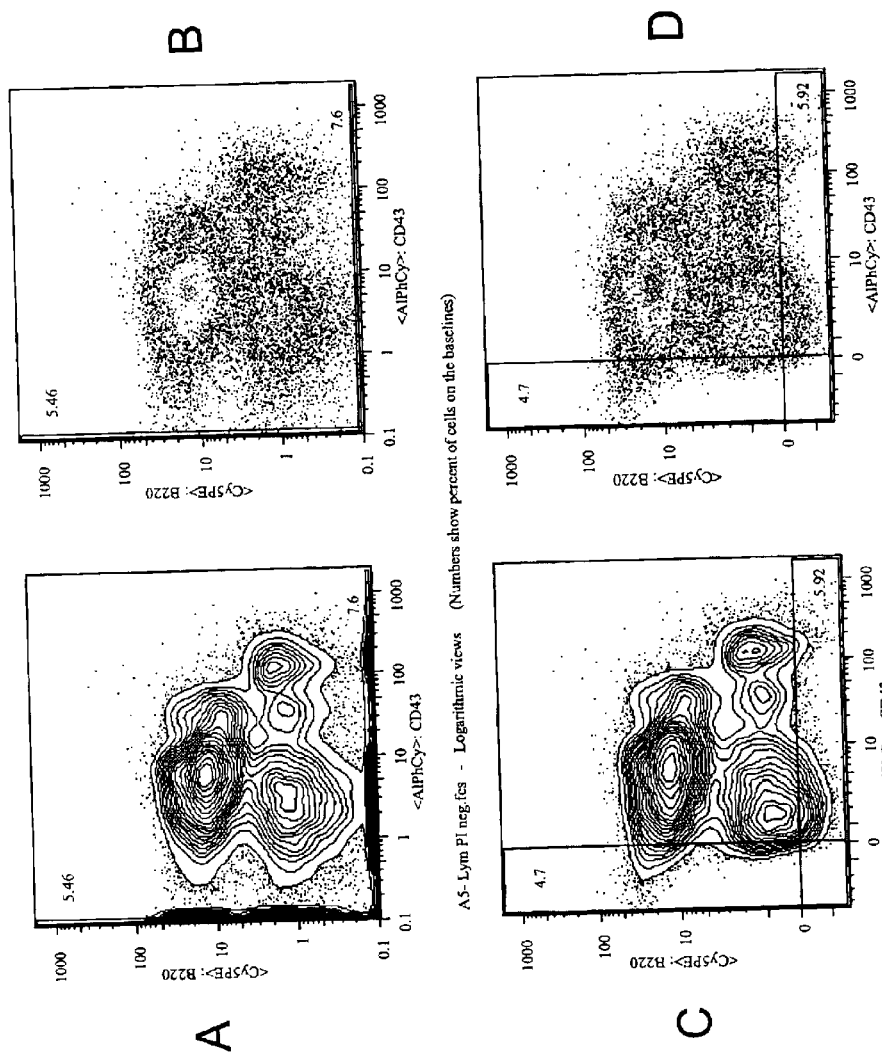
FIGS. 8A–D show log and logical displays of data with about 11% negatives.

FIGS. 4–8 illustrate the results comparing log displays with Logicle displays of the same data. FIGS. 4A–C show plots blank bead data from the BD digital electronics with floating point export so that the "picket fence" effect is eliminated and even the negative area signals are properly represented. Note, the negative values visible in FIG. 4C. FIGS. 5A–D show single stain control data with a median line drawn in. The Logicle representation shows the matched centering but greater vertical dimension spread in the positive population. FIGS. 6A and B show very smeary, low photon red-red data in which the log view is quite deceptive. FIGS. 7 A–D and FIGS. 8A–D show how the edge data populations in the log plots are really just ordinary parts of the adjacent populations.

The computed compensation on linear data is best if resolution is adequate. Computed compensation on uncompensated logamp data is good if log scaling is reasonably accurate. Analog compensation on all instruments tested leads to overcompensation and signal estimate distortion. Log display of computed compensation data cannot represent the full data range and promotes incorrect interpretations of cell populations. The Logicle-BiExponential display method of the invention does a much better job of representing multicolor FACS data in a way that facilitates correct interpretation and accurate delineation of cell populations.

Exemplary Function Constructed for Data Display

As described above, the function constructed for data display (e.g., FACS data display, etc.) starts with the sinh function:

$$\sinh(x)=(e^x-e^{-x})/2$$

This can be generalized as a biexponential function:

$$v(x;a,b,c,d,k)=ae^{bx}-ce^{-dx}+k$$

The specifications and constraints (V and V''=0 at x=0) lead to:

$$V=a(e^x-p^2e^{-px}+p^2-1)$$

where V is the data value to be plotted at display position x in the plot, a is a scaling factor and p is the strength of the linearization. This is one embodiment of the "Logicle" function, referred to above.

One way to express the Logicle function for data value "V" is using two parameters, an overall scaling "a" and a linearization parameter "p", and the display variable "x". The linearization width "w", referred to above, is w=2p*ln(p)/(p+1). The plain hyperbolic sine function has p=1<=>w=0. For high values of p, w approaches 2ln(p).

In order to increase the range of data values in the relatively linear zone around zero, we can increase the overall scale factor "a" or increase "p" (increase "w"). In one implementation of certain aspects of the invention (Logicle 1.1 and FlowJo4.3 available on the world wide web at flowjo.com) the need for increased near-linear range is accommodated with a balanced increase in both the overall scaling and in "w". For example, if we had a Logicle function with parameters $a_1$ and $w_1$ and wanted a new function to accommodate 4 times the data range in the relatively linear zone we would adjust each parameter to cover 2 times the range so that the total adjustment would be 2×2=4. This would lead to a2=2*$a_1$ and $w_2$=$w_1$+ln(2). This is functionally the same as described above using dilation D and w and $x_1$.

Figure 9:
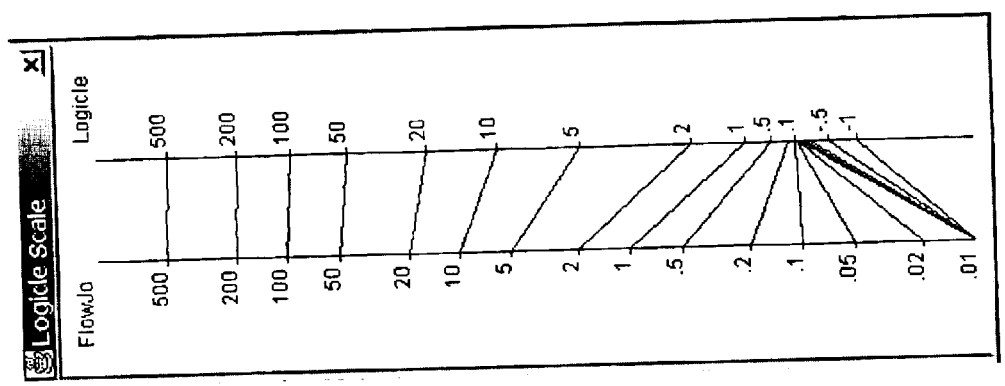
FIG. 9 shows a display screen according to one embodiment of the present invention.
Figure 10:
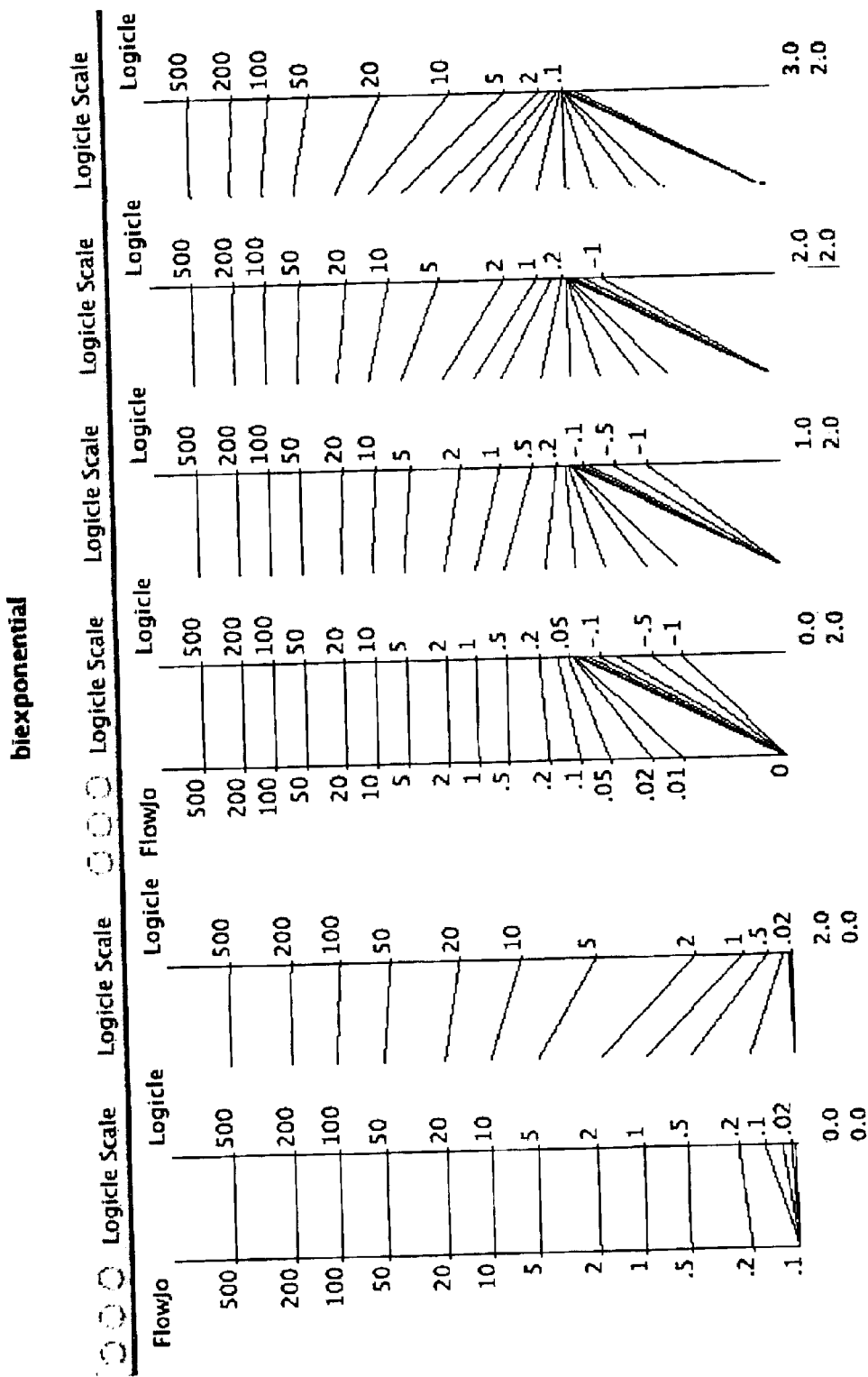
FIG. 10 shows a display screen that depicts a comparison of logarithmic scaling ("FlowJo" label) with Logical scales using different linearization widths "W" (the upper number below each Logical scale).

Aspects of the Logicle function are further illustrated in the figures. For example, FIG. 9 shows a display screen according to one embodiment of the present invention. Note, that depending one the choice of parameters the program can provide a range of behaviors with similar properties but this example exhibits the general features of the method and how it differs from an ordinary logarithmic scale. To further illustrate, FIG. 10 shows a display screen that depicts a comparison of logarithmic scaling ("FlowJo" label) with Logicle scales using different linearization widths "W" (the upper number below each Logicle scale). In particular, this is a composite version of six Logicle scales. There are two display variables below each Logicle scale. The upper one relates to the strength of the linearization. The lower one adjusts the amount of space on the scale allocated to negative data values so that, for a value of zero, the data zero is at the bottom of the scale and, for a value of 2, negative values get space corresponding to 2 decades in the upper logarithmic region.

Figure 11:
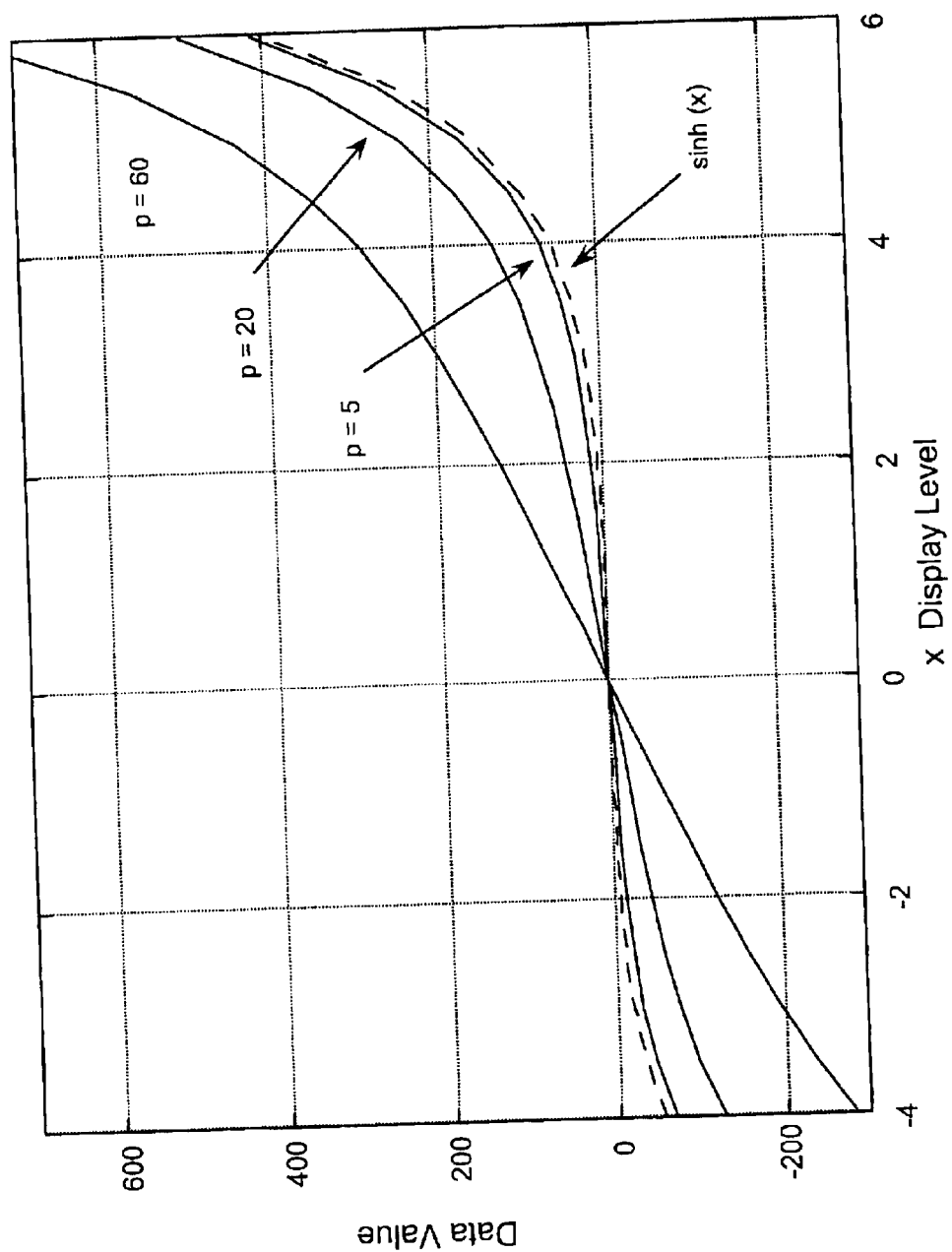
FIG. 11 shows plots of Logical functions with different "p" values.
Figure 12:
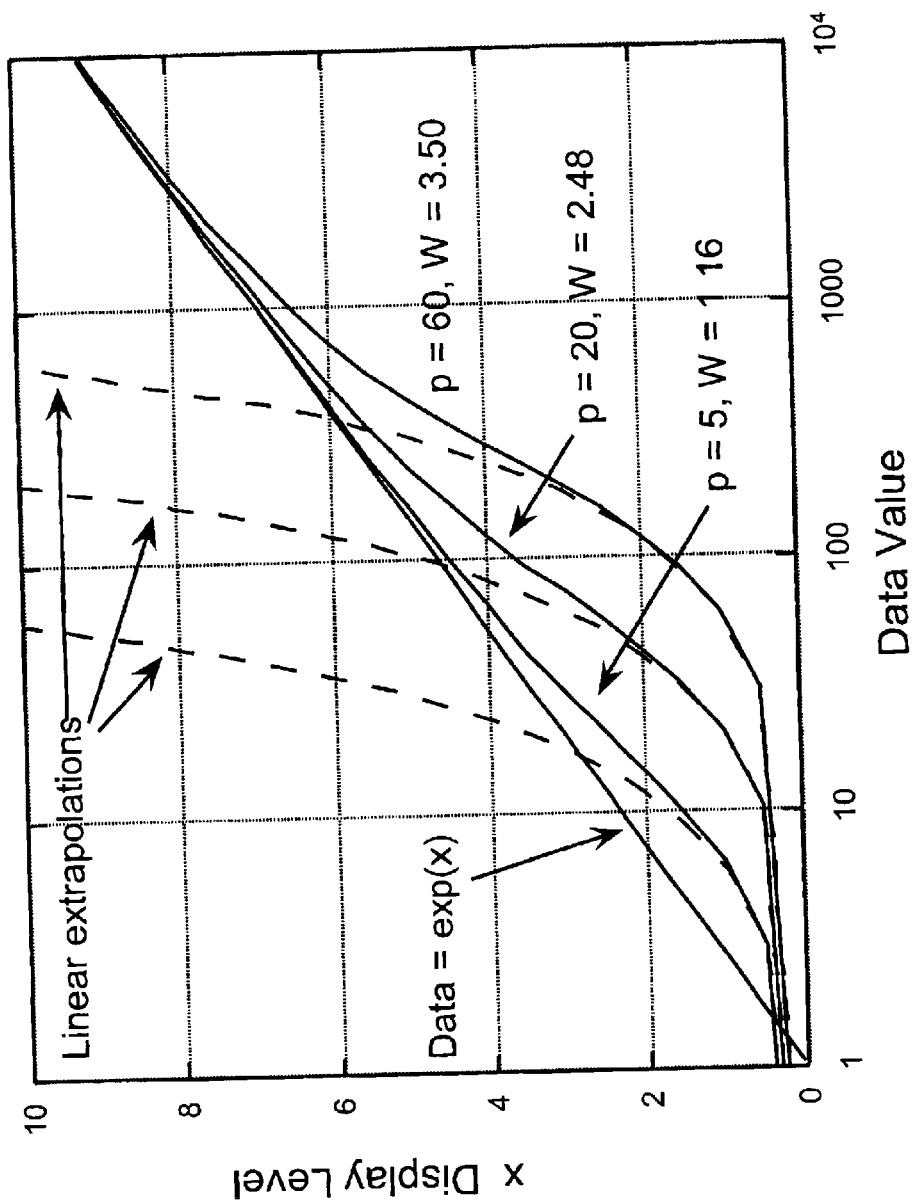
FIG. 12 shows plots illustrating Logical functions in relation to linear and log asymptotes.

FIG. 11 shows plots of Logicle functions with different "p" values. Sin h(x) corresponds to p=0. FIG. 12 shows plots illustrating how Logicle functions stay close to corresponding pure linear functions (dashed lines) for low data values and move over to being close to pure log (data=exp(x)) for high data values. The "W" values shown in the figure are just base 10 versions of the "w" discussed above so that W=w/ln(10).

Figure 13:
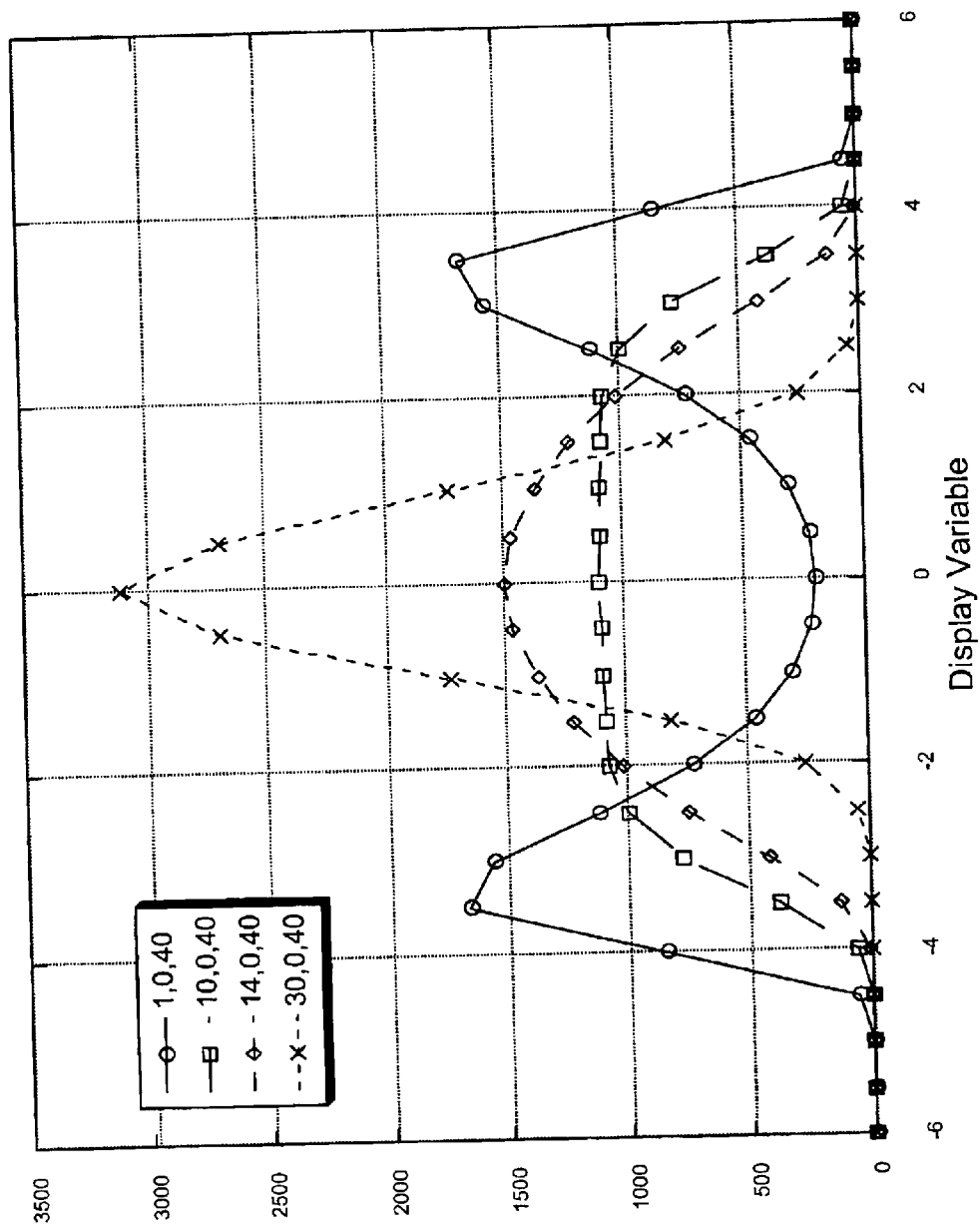
FIG. 13 is a plot that shows normal distributions displayed with different Logical width parameters 1.
Figure 14:
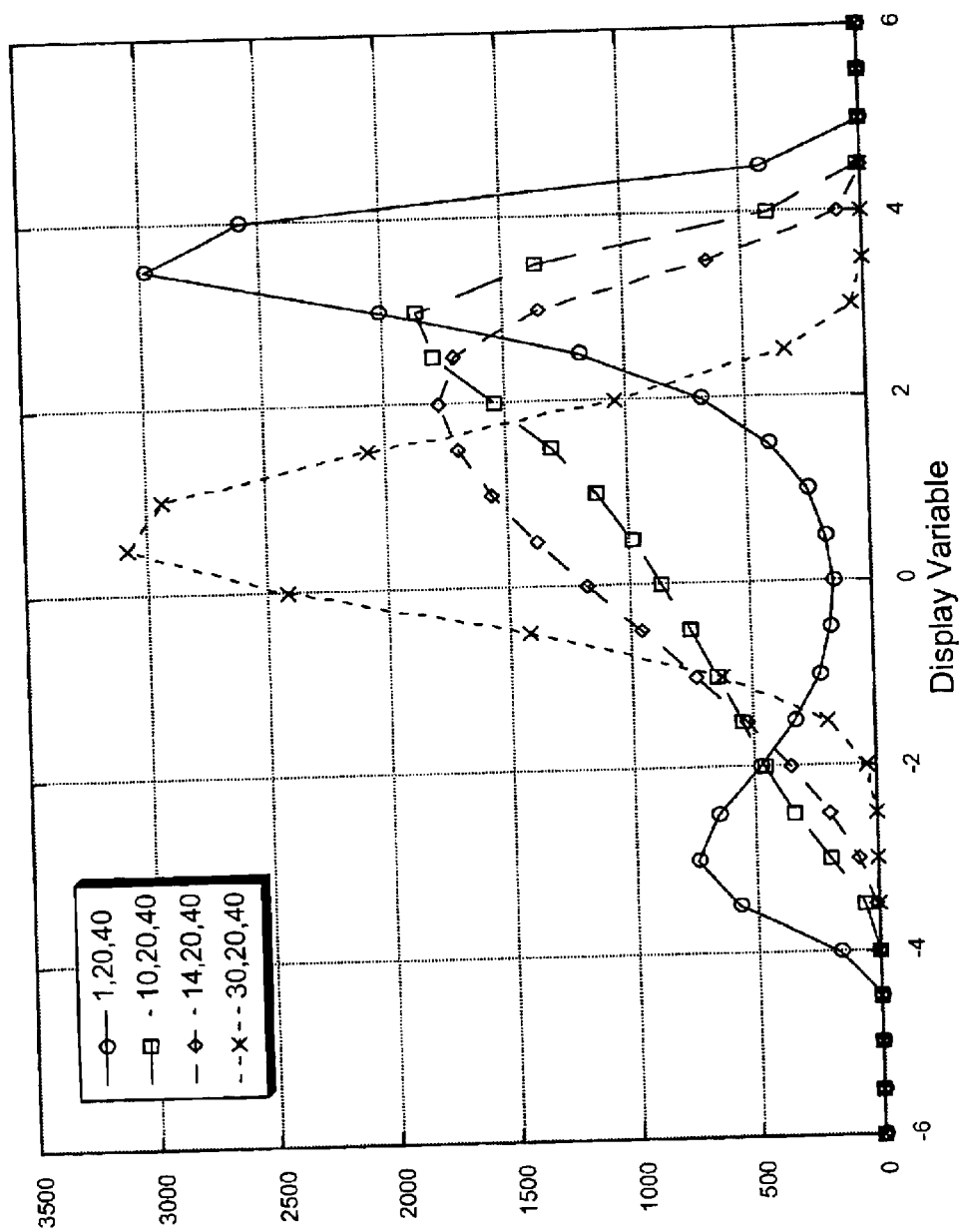
FIG. 14 is a plot that shows normal distributions displayed with different Logical width parameters 2.
Figure 15:
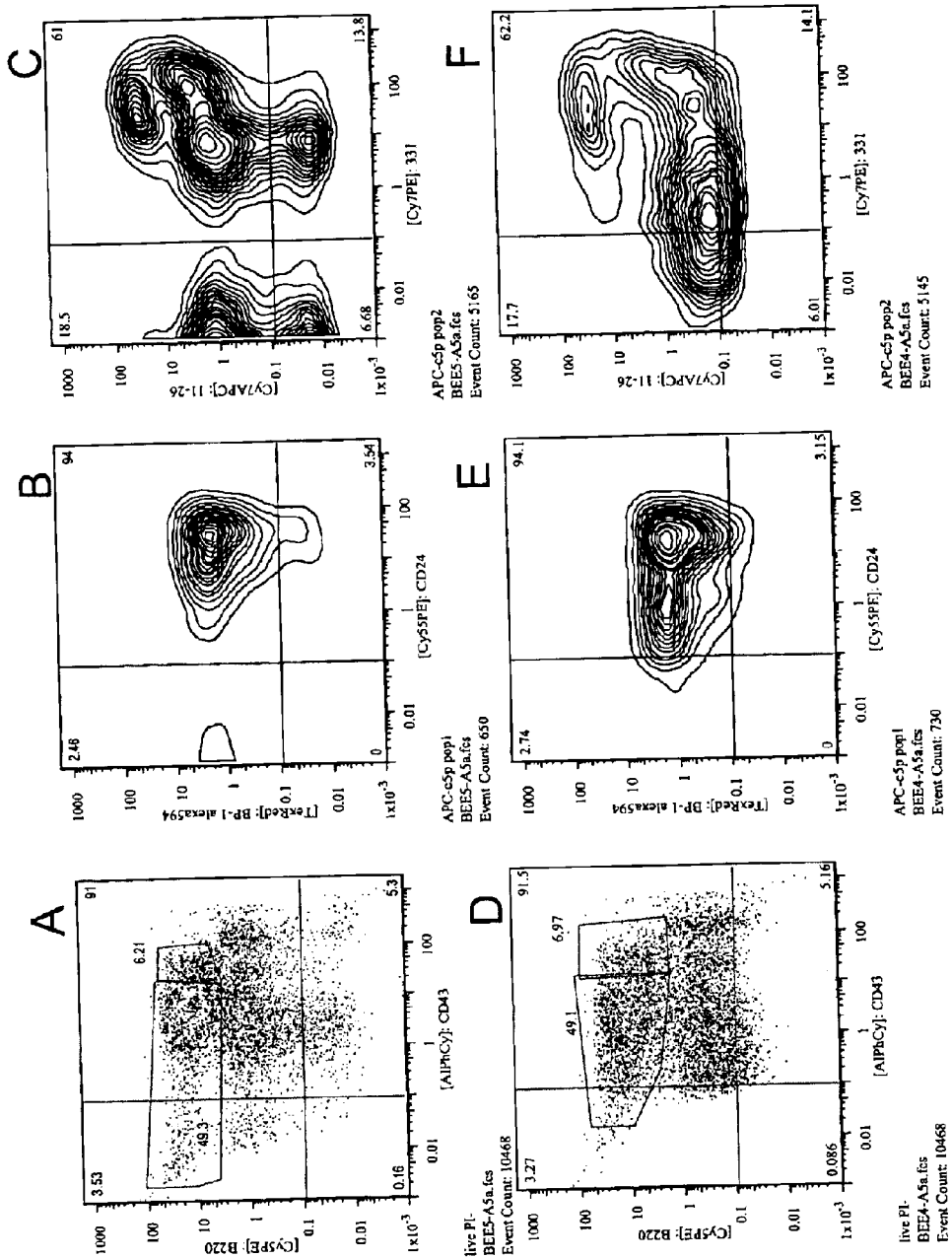
FIGS. 15A–F are plots showing multicolor cell data.
Figure 16:
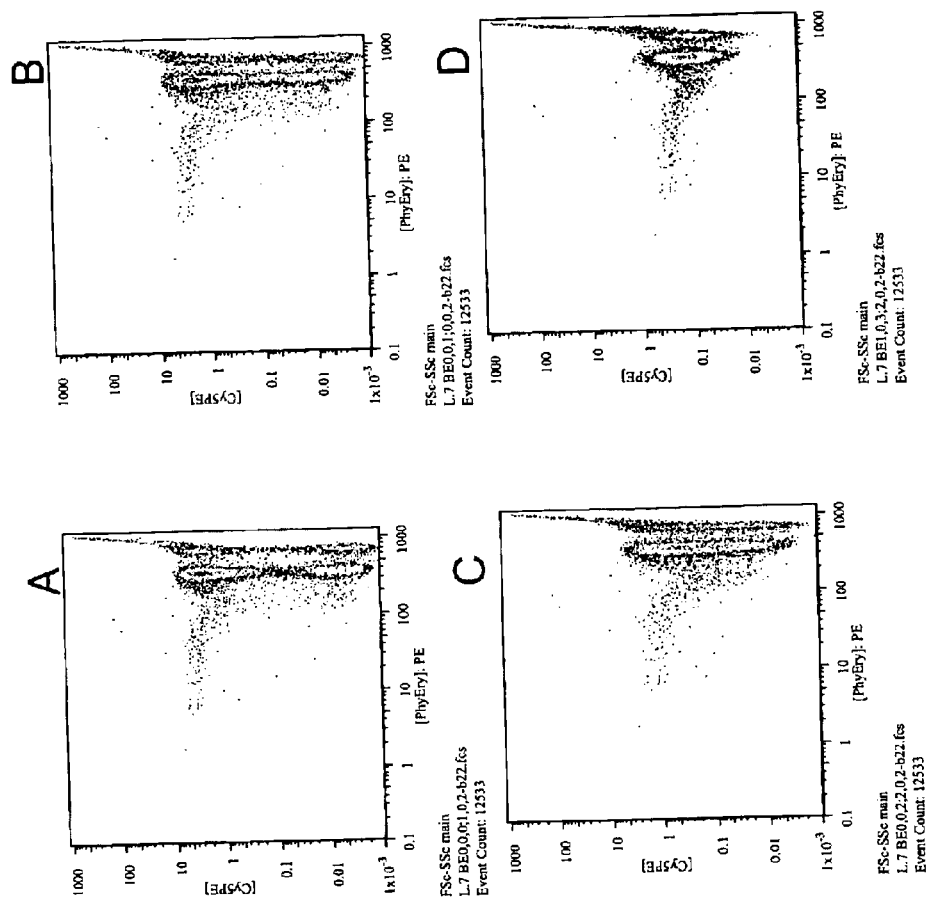
FIGS. 16A–D are plots showing a single set of test particle data with different linearization strengths.

FIG. 13 is a plot that shows normal distribution with mean zero displayed with different Logical scalings. If "p" is too low (e.g. p=1) the display "breaks up" into two apparent peaks. This is the kind of display behavior that is typically to be avoided. For p=10 the display is flat topped but not bi-modal. For p=14 the display is clearly unimodal—this is approximately the minimum linearization that would be considered desirable. For p=30 the display is close to linear over the main part of the distribution, so the display looks visually like a normal distribution. FIG. 14 is the same plot as FIG. 13 except that the normal distribution has a mean of 20 rather than 0.

To further illustrate aspects of the invention, FIGS. 15A–F are plots showing multicolor cell data. The upper row (FIGS. 15A–C) show minimum linearization, and what is to the upper right of the crosshairs (which indicate the zeros in the two dimensions) is close to what would be seen in an ordinary log plot. The lower row (FIGS. 15 D–F) show the same data displayed with stronger transformation as appropriate for the particular data dimensions. FIGS. 16A–D are plots showing a single set of test particle data with different linearization strengths (W=0, 1, 2 and 3) in the vertical dimension. The logarithmic scales shown in FIGS. 15 and 16 do not represent the actual Logicle scales used to generate the displays.

Figure 17:
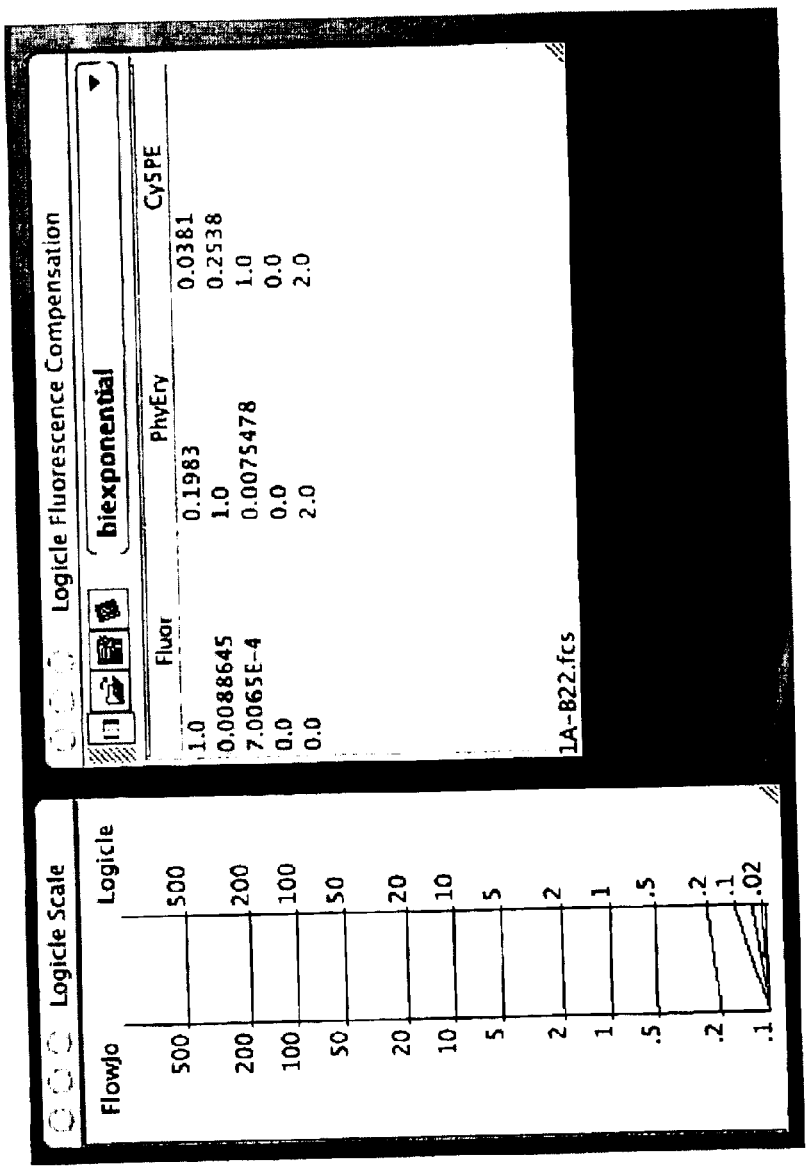
FIG. 17 is a display screen of a program window and a scale illustration according to one embodiment of the invention.
Figure 18:
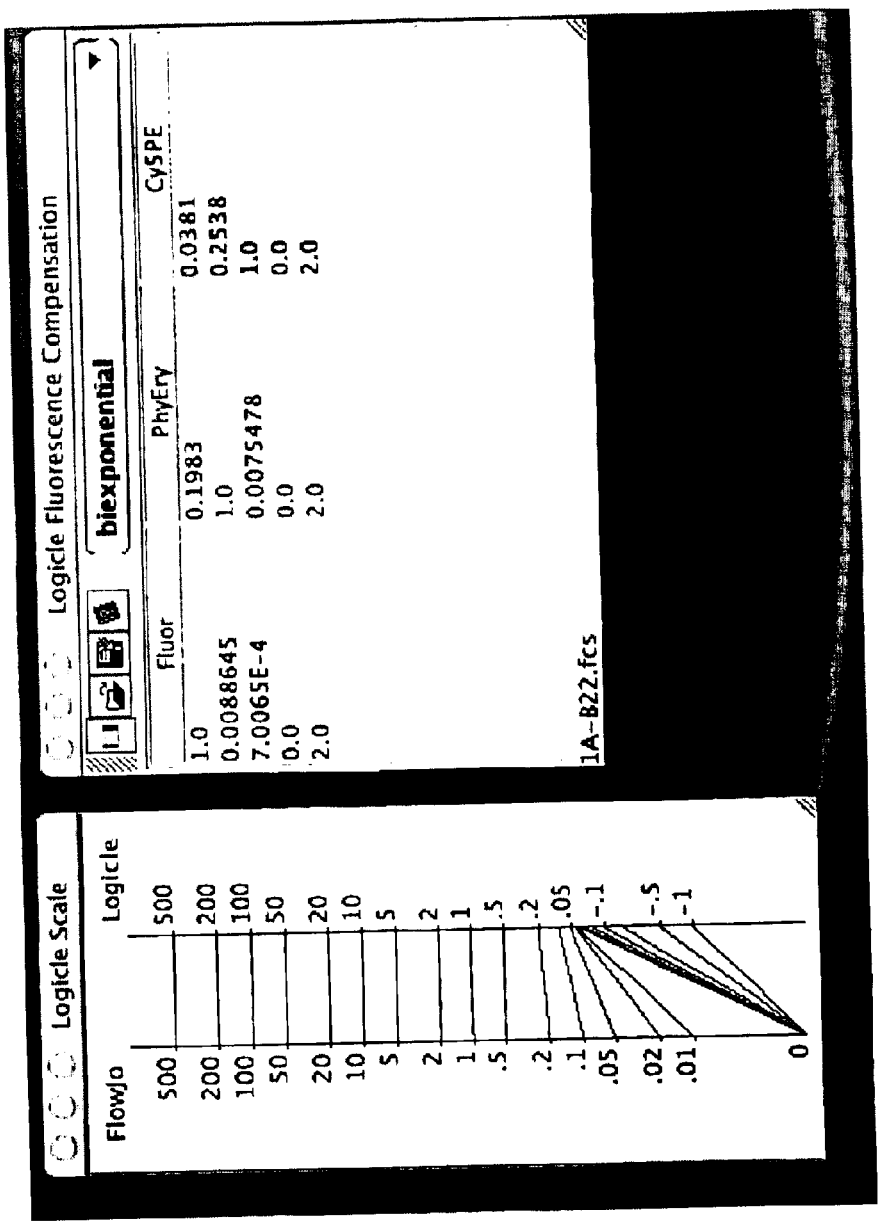
FIG. 18 is a display screen of a program window and a scale illustration according to one embodiment of the invention.
Figure 19:
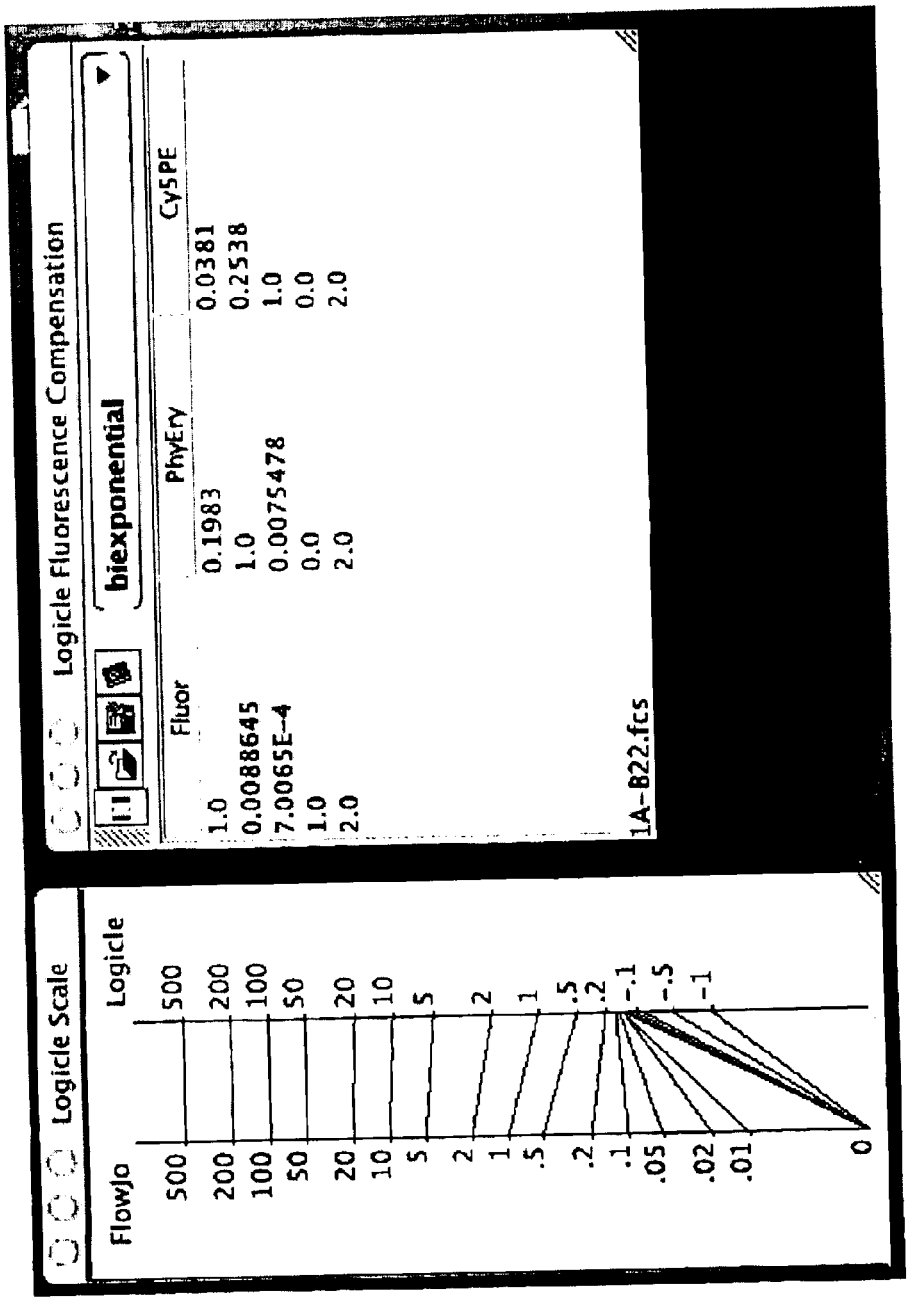
FIG. 19 is a display screen of a program window and a scale illustration according to one embodiment of the invention.
Figure 20:
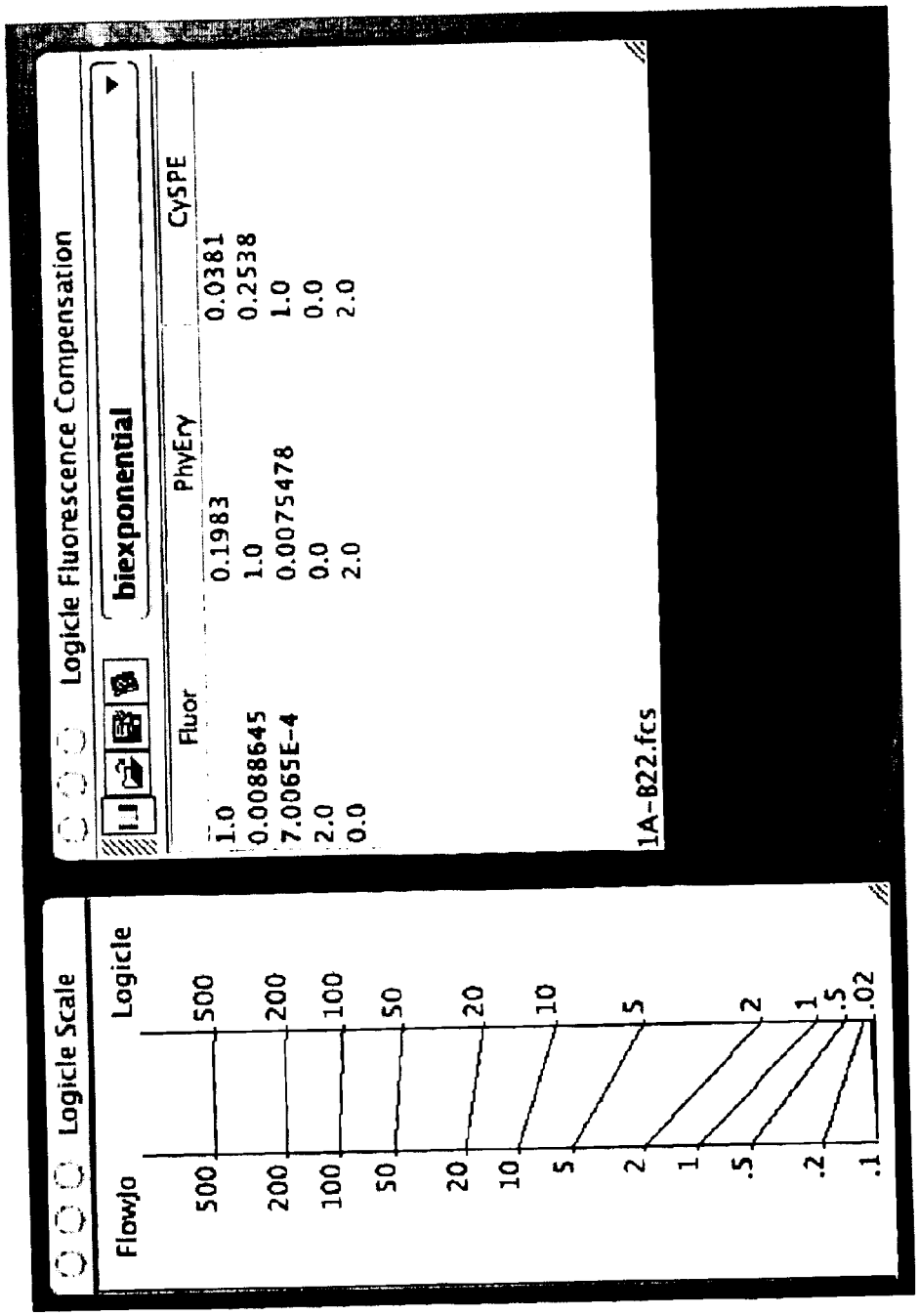
FIG. 20 is a display screen of a program window and a scale illustration according to one embodiment of the invention.
Figure 21:
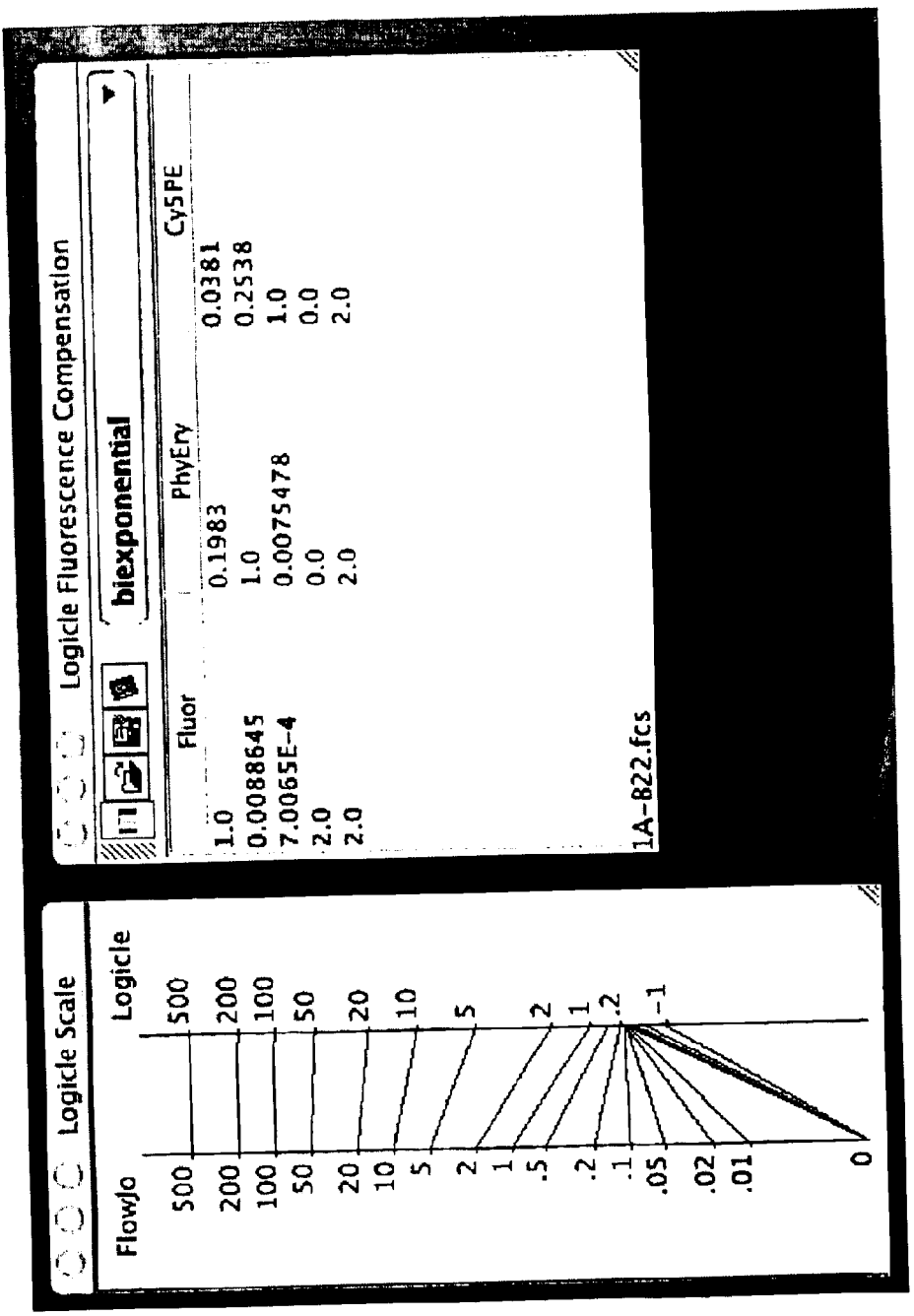
FIG. 21 is a display screen of a program window and a scale illustration according to one embodiment of the invention.
Figure 22:
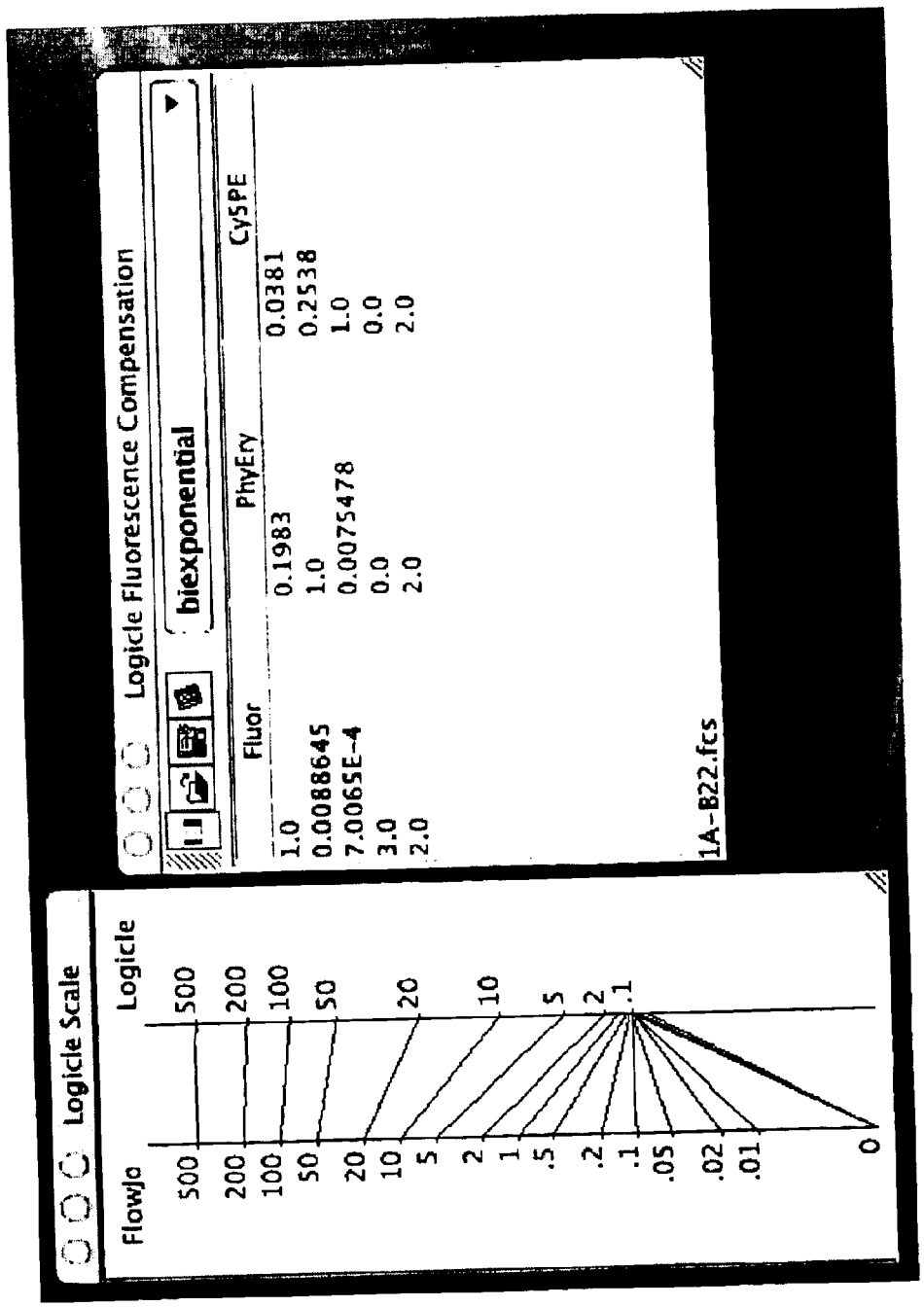
FIG. 22 is a display screen of a program window and a scale illustration according to one embodiment of the invention.

FIGS. 17–22 are display screens of program windows and scale illustrations. The right side scale in each nomogram is what would be the edge scale on a piece of graph paper used to plot the data. In FIG. 17, the strength of the linearization around zero is 0, and the number of "decades" of space added on the negative side is 0. In FIG. 18, the strength of the linearization around zero is 0, and the number of "decades" of space added on the negative side is 2. In FIG. 19, the strength of the linearization around zero is 1, and the number of "decades" of space added on the negative side is 2. In FIG. 20, the strength of the linearization around zero is 2, and the number of "decades" of space added on the negative side is 0. In FIG. 21, the strength of the linearization around zero is 2, and the number of "decades" of space added on the negative side is 2. In FIG. 22, the strength of the linearization around zero is 3, and the number of "decades" of space added on the negative side is 2.

Another Exemplary Function Constructed for Data Display

As above, the function constructed for data display (e.g., FACS data display, etc.) starts with the sinh function:

$$\sinh(x)=(e^x-e^{-x})/2$$

This is generalized and expressed in base 10 as:

$$V=a(10^{bx})-c(10^{-dx})+k$$

The specifications and constraints (V and V"=0 at x=0) lead to:

$$V=Z(10^{n/m}-G^2(10^{-n/mG}-1)$$

where V is the data value to be displayed at channel position n in the plot, m is the asymptotic channels per decade, and G is the strength of the linearization. Note, that this is a version of the function in terms used for display of flow cytometry data. The family of related functions is produced for different values of G.

Figure 23:
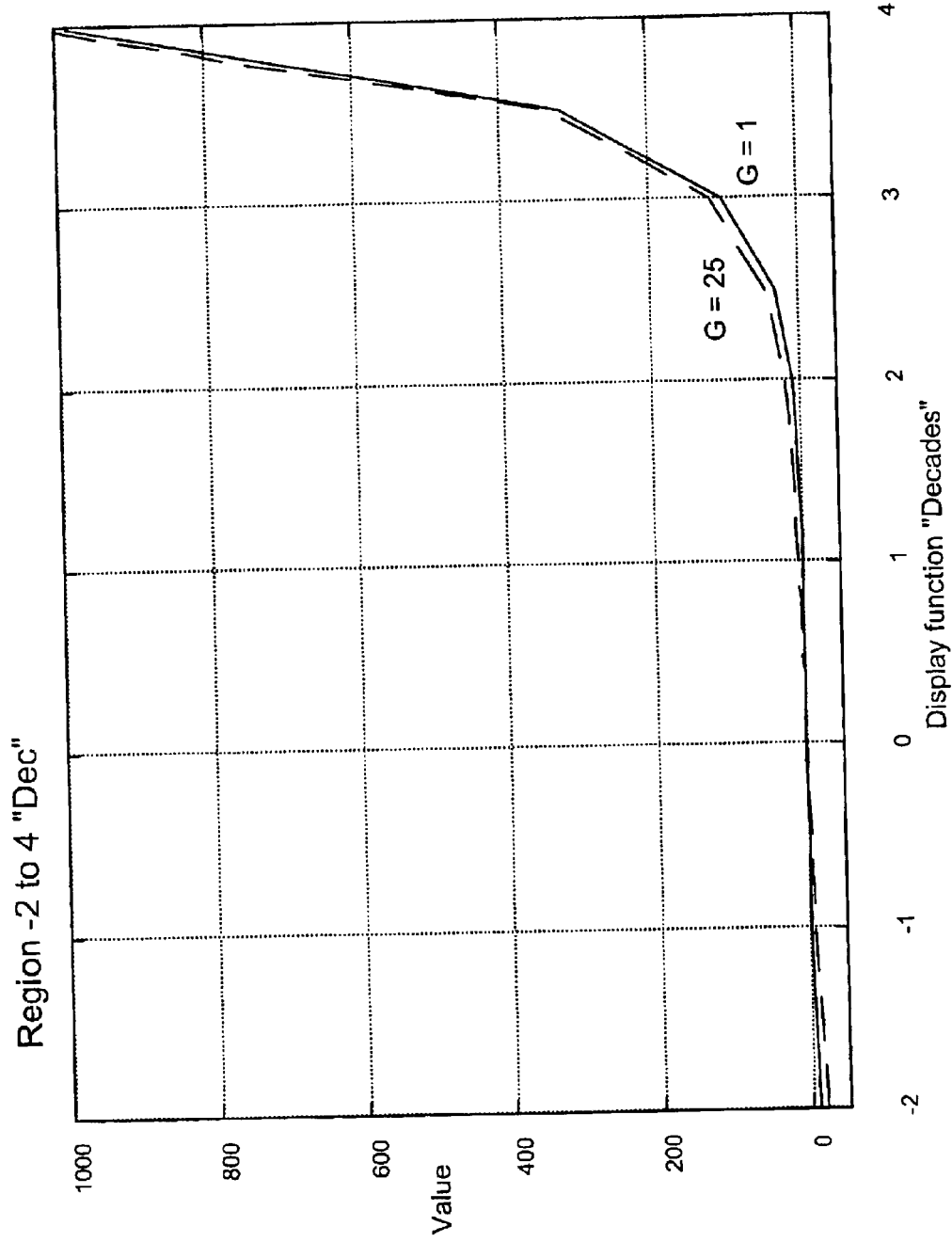
FIG. 23 is a plot (Region –2 to 4) of a scaling function for different linearization strengths showing at what point in a display scale (horizontal) a particular data value (vertical) would be plotted.
Figure 24:
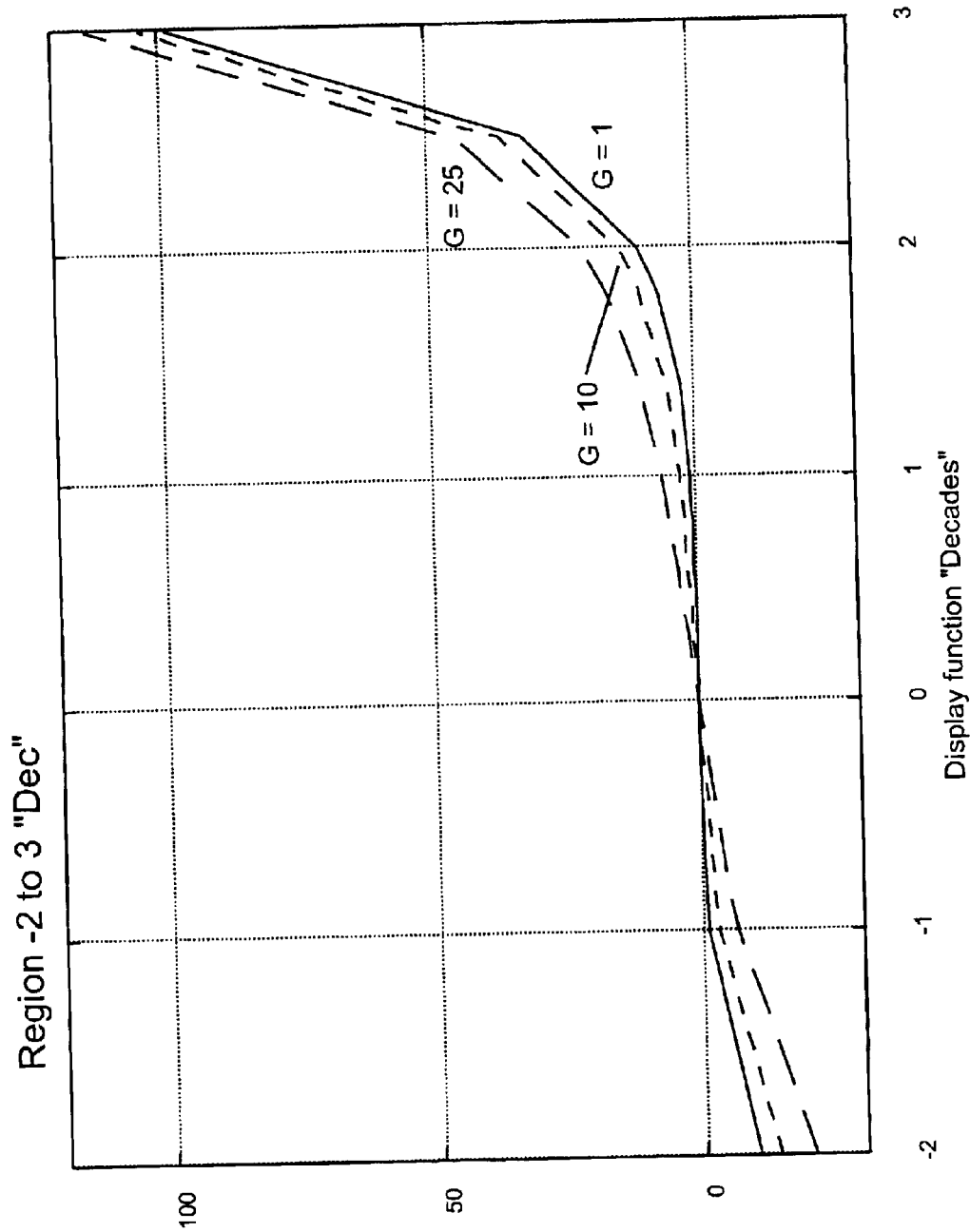
FIG. 24 is a plot of a scaling function illustrated over narrower ranges (Region –2 to 3) than the plot depicted in FIG. 23 to show details of how the function behaves for different linearization strengths.
Figure 25:
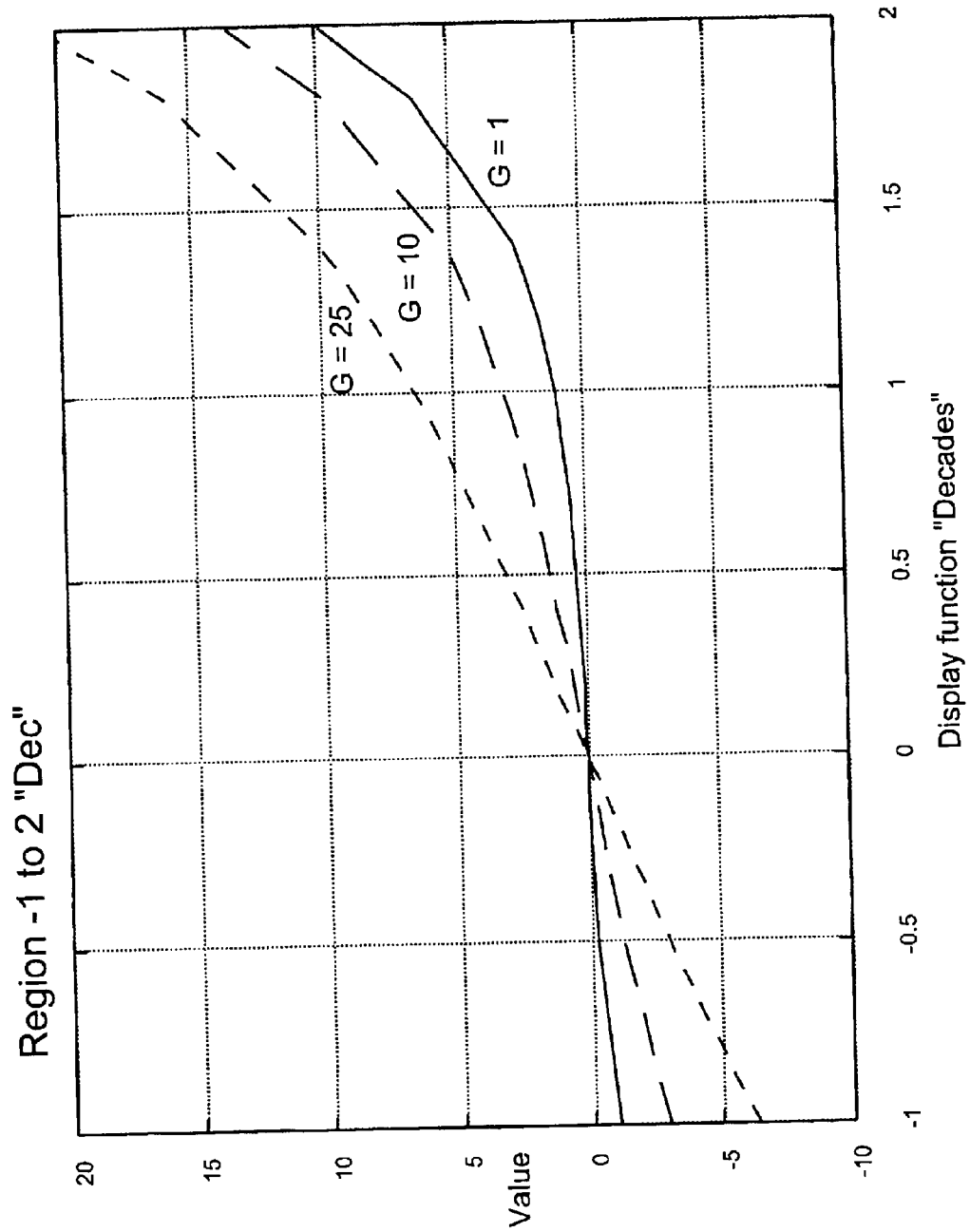
FIG. 25 is another plot of a scaling function illustrated over narrower ranges (Region –1 to 2) than the plot depicted in FIG. 23 to show details of how the function behaves for different linearization strengths.
Figure 26:
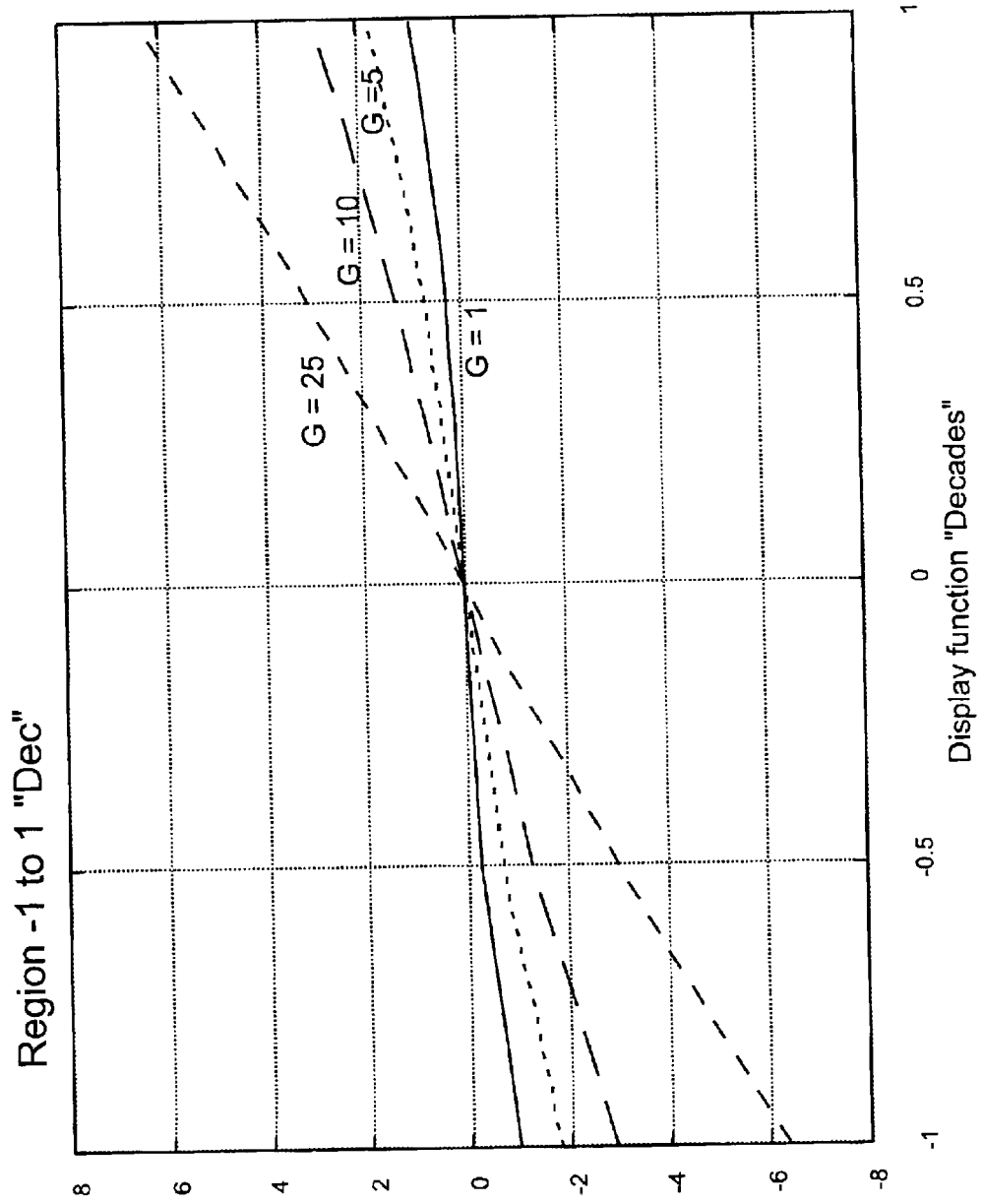
FIG. 26 is another plot of a scaling function illustrated over narrower ranges (Region –1 to 1) than the plot depicted in FIG. 23 to show details of how the function behaves for different linearization strengths.

To further illustrate, FIG. 23 is a plot (Region −2 to 4) of a scaling function for different linearization strengths showing at what point in a display scale (horizontal) a particular data value (vertical) would be plotted. FIG. 24 is a plot of a scaling function illustrated over narrower ranges (Region −2 to 3) than the plot depicted in FIG. 23 to show details of how the function behaves for different linearization strengths. FIG. 25 is another plot of a scaling function illustrated over narrower ranges (Region −1 to 2) than the plot depicted in FIG. 23 to show details of how the function behaves for different linearization strengths. FIG. 26 is another plot of a scaling function illustrated over narrower ranges (Region −1 to 1) than the plot depicted in FIG. 23 to show details of how the function behaves for different linearization strengths.

Web Site Embodiment

The methods of this invention can be implemented in a localized or distributed computing environment. For example, in one embodiment featuring a localized computing environment, a flow cytometry system is operably linked to a computational device equipped with user input and output features. In a distributed environment, the methods can be implemented on a single computer, a computer with multiple processes or, alternatively, on multiple computers. The computers can be linked, e.g., through a shared bus, but more commonly, the computer(s) are nodes on a network. The network can be generalized or dedicated, at a local level or distributed over a wide geographic area. In certain embodiments, the computers are components of an intra-net or an internet.

In such use, typically, a client (e.g., a scientist, a patient, practitioner, provider, or the like) executes a Web browser and is linked to a server computer executing a Web server. The Web browser is, for example, a program such as IBM's Web Explorer, Internet explorer, NetScape or Mosaic, or the like. The Web server is typically, but not necessarily, a program such as IBM's HTTP Daemon or other WWW daemon (e.g., LINUX-based forms of the program). The client computer is bi-directionally coupled with the server computer over a line or via a wireless system. In turn, the server computer is bi-directionally coupled with a website (server hosting the website) providing access to software implementing the methods of this invention. A user of a client connected to the Intranet or Internet may cause the client to request resources that are part of the web site(s) hosting the application(s) providing an implementation of the methods of this invention. Server program(s) then process the request to return the specified resources (assuming they are currently available). A standard naming convention has been adopted, known as a Uniform Resource Locator ("URL"). This convention encompasses several types of location names, presently including subclasses such as Hypertext Transport Protocol ("http"), File Transport Protocol ("ftp"), gopher, and Wide Area Information Service ("WAIS"). When a resource is downloaded, it may include the URLs of additional resources. Thus, the user of the client can easily learn of the existence of new resources that he or she had not specifically requested.

Methods of implementing Intranet and/or Intranet embodiments of computational and/or data access processes are well known to those of skill in the art and are documented, e.g., in ACM Press, pp. 383–392; ISO-ANSI, Working Draft, "Information Technology-Database Language SQL", Jim Melton, Editor, International Organization for Standardization and American National Standards Institute, Jul. 1992; ISO Working Draft, "Database Language SQL-Part 2: Foundation (SQL/Foundation)", CD9075-2:199.chi.SQL, Sep. 11, 1997; and Cluer et al. (1992) A General Framework for the Optimization of Object-Oriented Queries, Proc SIGMOD International Conference on Management of Data, San Diego, Calif., Jun. 2–5, 1992, SIGMOD Record, vol. 21, Issue 2, Jun., 1992; Stonebraker, M., Editor. Other resources are available, e.g., from Microsoft, IBM, Sun and other software development companies.

Example Web Interface for Accessing Data Over a Network

Figure 27A:
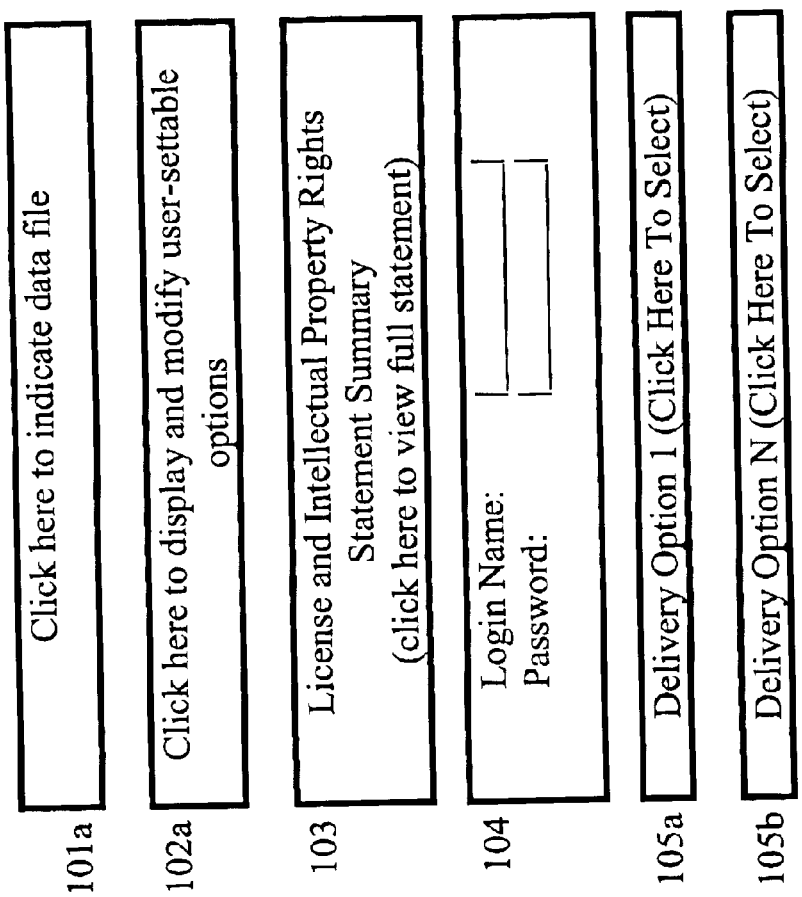
FIGS. 27A and B illustrate example interfaces for obtaining data analysis using a computer interface, possibly over a web page, according to specific embodiments of the present invention.

FIGS. 27 A and B illustrate example interfaces for obtaining data analysis using a computer interface, possibly over a web page, according to specific embodiments of the present invention. FIG. 27A illustrates the display of a Web page or other computer interface for requesting statistical analysis. According to specific implementations and/or embodiments of the present invention, this example interface is sent from a server system to a client system when a user accessed the server system. This example Web page contains an input selection 101, allowing a user to specify input data. As will be understood in the art, each selection button can activate a set of cascading interface screens that allows a user to select from other available options or to browse for an input file. According to specific embodiments of the present invention, option selection 102 can also be provided, allowing a user to modify the user settable options discussed herein. A licensing information section 103 and user identification section 104 can also be included. One skilled in the art would appreciate that these various sections can be omitted or rearranged or adapted in various ways. The 104 section provides a conventional capability to enter account information or payment information or login information. (One skilled in the art would appreciate that a single Web page on the server system may contain all these sections but that various sections can be selectively included or excluded before sending the Web page to the client system.)

FIG. 27B illustrates the display of an interface confirming a request. The confirming Web page can contain various information pertaining to the order and can optionally include a confirmation indication allowing a user to make a final confirmation to proceed with the order. For particular systems or analysis, this page may also include warnings regarding use of proprietary data or methods and can include additional license terms, such as any rights retained by the owner of the server system in either the data.

EMBODIMENT IN A PROGRAMMED INFORMATION APPLIANCE

Figure 28:
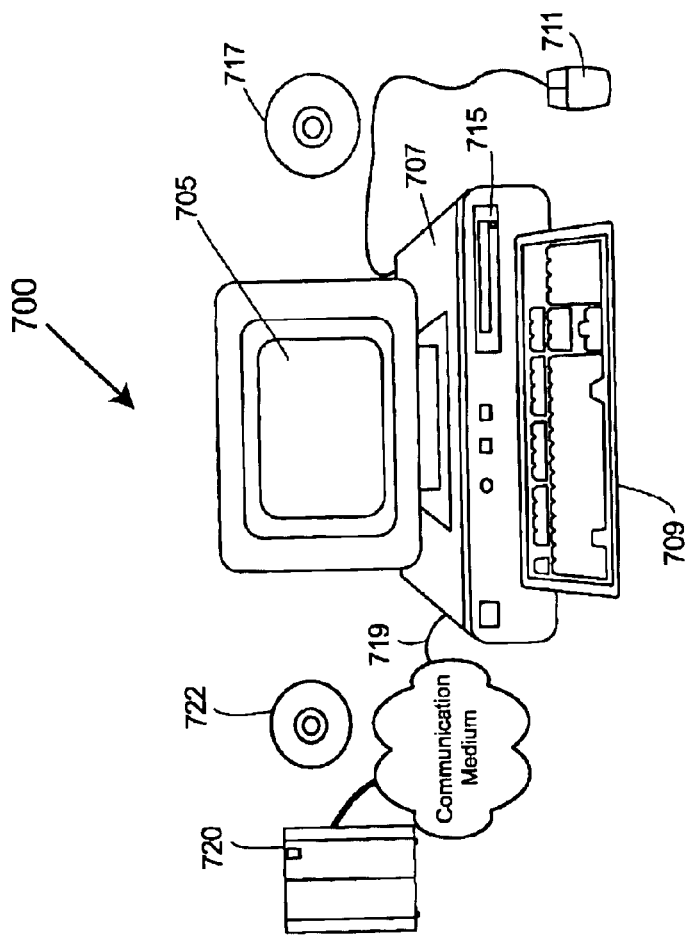
FIG. 28 is a block diagram showing a representative example logic device in which various aspects of the present invention may be embodied.

FIG. 28 is a block diagram showing a representative example logic device in which various aspects of the present invention may be embodied. As will be understood to practitioners in the art from the teachings provided herein, the invention can be implemented in hardware and/or software. In some embodiments of the invention, different aspects of the invention can be implemented in either client-side logic or server-side logic. As will be understood in the art, the invention or components thereof may be embodied in a fixed media program component containing logic instructions and/or data that when loaded into an appropriately configured computing device cause that device to perform according to the invention. As will be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

FIG. 28 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711, disk drives 715 and optional monitor 705. Fixed media 717, or fixed media 722 over port 719, may be used to program such a system and may represent a disk-type optical or magnetic media, magnetic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection.

The invention also may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

Integrated Systems

Integrated systems, e.g., for performing FACS assays and data analysis, as well as for the compilation, storage and access of databases, typically include a digital computer with software including an instruction set as described herein, and, optionally, one or more of high-throughput sample control software, image analysis software, other data interpretation software, a robotic control armature for transferring solutions from a source to a destination (such as a detection device) operably linked to the digital computer, an input device (e.g., a computer keyboard) for entering subject data to the digital computer, or to control analysis operations or high throughput sample transfer by the robotic control armature. Optionally, the integrated system further comprises an image scanner for digitizing label signals from labeled assay components.

Readily available computational hardware resources using standard operating systems can be employed and modified according to the teachings provided herein, e.g., a PC (Intel x 86 or Pentium chip-compatible DOS™, OS2™, WINDOWS™, WINDOWS NT™, WINDOWS95™, WINDOWS98™, WINDOWS2000™, WINDOWS XP™, LINUX, or even Macintosh, Sun or PCs will suffice) for use in the integrated systems of the invention. Current art in software technology is adequate to allow implementation of the methods taught herein on a computer system. Thus, in specific embodiments, the present invention can comprise a set of logic instructions (either software, or hardware encoded instructions) for performing one or more of the methods as taught herein. For example, software for providing the described data and/or statistical analysis can be constructed by one of skill using a standard programming language such as Visual Basic, Fortran, Basic, Java, or the like. Such software can also be constructed utilizing a variety of statistical programming languages, toolkits, or libraries.

Various programming methods and algorithms, including genetic algorithms and neural networks, can be used to perform aspects of the data collection, correlation, and storage functions, as well as other desirable functions, as described herein. In addition, digital or analog systems such as digital or analog computer systems can control a variety of other functions such as the display and/or control of input and output files. Software for performing the statistical methods of the invention, such as programmed embodiments of the statistical methods described above, are also included in the computer systems of the invention. Alternatively, programming elements for performing such methods as principle component analysis (PCA) or least squares analysis can also be included in the digital system to identify relationships between data. Exemplary software for such methods is provided by Partek, Inc., St. Peter, Mo; on the world wide web at partek.com. Optionally, the integrated systems of the invention include an automated workstation.

Automated and/or semi-automated methods for solid and liquid phase high-throughput sample preparation and evaluation are available, and supported by commercially available devices. For example, robotic devices for preparation of nucleic acids from bacterial colonies, e.g., to facilitate production and characterization of the libraries of candidate genes include, for example, an automated colony picker (e.g., the Q-bot, Genetix, U.K.) capable of identifying, sampling, and inoculating up to 10,000/4 hrs different clones into 96 well microtiter dishes. Alternatively, or in addition, robotic systems for liquid handling are available from a variety of sources, e.g., automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Beckman Coulter, Inc. (Fullerton, Calif.)) which mimic the manual operations performed by a scientist. Any of the above devices are suitable for use with the present invention, e.g., for high-throughput analysis of library components or subject leukocyte samples. The nature and implementation of modifications to these devices (if any) so that they can operate as discussed herein will be apparent to persons skilled in the relevant art.

A variety of commercially available peripheral equipment, including, e.g., flow cytometers and related optical and fluorescent detectors, and the like, and software are available for digitizing, storing and analyzing a digitized video or digitized optical or other assay results using a computer. Commerical Suppliers of flow cytometry instrumentation include Beckman Coulter, Inc. (Fullerton, Calif.) among many others.

Example System Embodiment

Figure 29:
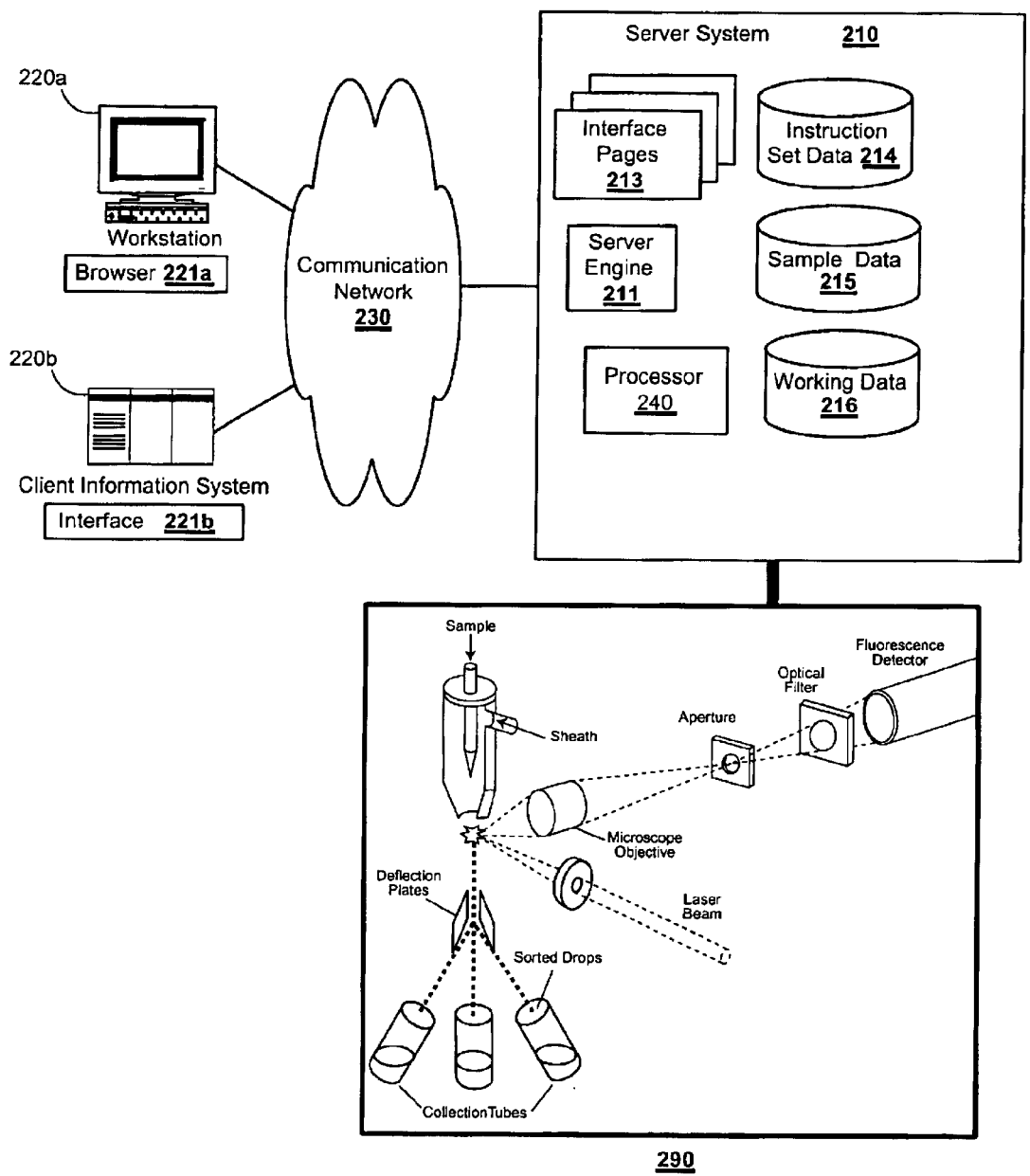
FIG. 29 is a block diagram illustrating an integrated system according to specific embodiments of the present invention.

FIG. 29 is a block diagram illustrating an integrated system according to specific embodiments of the present invention. This particular example embodiment optionally supports providing statistical analysis over a network. The server system 210 includes a server engine 211, various interface pages 213, data storage 214 for storing instructions, data storage 215 for storing sample data, and data storage 216 for storing data generated by the computer system 210. According to specific embodiments of the invention, the server system further includes or is in communication with a processor 240 that further comprises one or more logic modules for performing one or more methods as described herein.

Optionally, one or more client systems may also comprise any combination of hardware and/or software that can interact with the server system. These systems may include digital workstation or computer systems (an example of which is shown as 220a) including a logic interface module (such as 221a) and/or various other systems or products through which data and requests can be communicated to a server system. These systems may also include laboratory-workstation-based systems (an example of which is shown as 220b) including a logic interface module (such as 221b) or various other systems or products through which data and requests can be communicated to a server system.

Optionally, the server computer 210 is in communication with or integrated with a flow cytometer system 290.

Other Embodiments

The invention has now been described with reference to specific embodiments. Other embodiments will be apparent to those of skill in the art. In particular, a viewer digital information appliance has generally been illustrated as a personal computer. However, the digital computing device is meant to be any information appliance for interacting with a remote data application, and could include such devices as a digitally enabled television, cell phone, personal digital assistant, etc.

Although the present invention has been described in terms of various specific embodiments, it is not intended that the invention be limited to these embodiments. Modification within the spirit of the invention will be apparent to those skilled in the art. In addition, various different actions can be used to effect the data analysis and/or display described herein. For example, a voice command may be spoken by the purchaser, a key may be depressed by the purchaser, a button on a client-side scientific device may be depressed by the user, or selection using any pointing device may be effected by the user.

It is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this application, including any references filed as part of an Information Disclosure Statement, are incorporated by reference in their entirety.

What is claimed is:

1. A method of analyzing data using a computer, said method comprising:
   receiving raw data at said computer;
   scaling said raw data using at least one scaling function that provides substantially linear transformations for data values proximal to zero and substantially logarithmic transformations for other data values to generate scaled data; and,
   using said scaled data to identify portions of said raw data of interest.

2. The method of claim 1, wherein said raw data comprises high dynamic range data.

3. A method of analyzing flow cytometry data using a computer, said method comprising:
   receiving raw data at said computer, said raw data comprising data from a plurality of light detectors of a flow cytometry system;
   scaling said raw data in said computer using at least one scaling function that provides substantially linear transformations for data values proximal to zero and substantially logarithmic transformations for other data values to generate scaled data; and,
   using said scaled data to identify portions of said raw data of interest.

4. The method of claim 3, wherein said scaling function transforms negative raw data values.

5. The method of claim 3, wherein a transition from linear to logarithmic scaling in said scaled data is substantially smooth.

6. The method of claim 3, wherein the second derivative of said scaling function is zero for a corresponding raw data value of zero.

7. The method of claim 3, wherein said scaling function comprises one or more optimization functions for viewing different raw data sets.

8. The method of claim 3, wherein said scaling function is substantially symmetrical proximal to a raw data value of zero.

9. The method of claim 3, wherein said flow cytometry system comprises a fluorescence-activated cell sorting flow cytometry system.

10. The method of claim 3, wherein said raw data is derived through fluorescence compensation.

11. The method of claim 3, wherein said scaling comprises specifying at least one preliminary parameter such that other variables are constrained by one or more criteria of said scaling function, thereby defining at least one single variable transformation.

12. The method of claim 11, wherein said single variable transformation comprises a family of related transformations.

13. The method of claim 3, wherein said using comprises inputting said scaled data into at least one data analysis algorithm to identify said portions of said raw data of interest.

14. The method of claim 13, wherein said data analysis algorithm comprises automated data analysis software.

15. The method of claim 3, wherein said using comprises displaying said scaled data for a human viewer.

16. The method of claim 15, wherein said scaled data is displayed on a coordinate grid and said scaling function primarily depends on data in a single data dimension, thereby assuring that said coordinate grid is substantially rectilinear.

17. The method of claim 15, wherein display values increase in size more than corresponding display variables in linear regions of said scaled data as a family-generating variable is adjusted to increase a range of linearity.

18. The method of claim 15, wherein said scaling function comprises at least one generalized hyperbolic sine function.

19. The method of claim 18, wherein said generalized hyperbolic sine function is a form of $V=Z(10^{n/m} -1-G^2(10^{-n/mG} -1))$, where V is a data value to be displayed at channel position n in a plot of said scaled data, m is the asymptotic channels per decade, and G is linearization strength.

20. The method of claim 18, wherein said generalized hyperbolic sine function is a form of $V=a(e^x-p^2e^{-px}+p^2-1)$, where V is a data value to be plotted at display position x in a plot, a is a scaling factor, and p is linearization strength.

21. The method of claim 18, wherein said generalized hyperbolic sine function is a form of $S(x; a, b, c, d, So)=ae^{bx}-ce^{-dx}-So$, for positive x and for negative x, a reflection of said positive x in a form of $Sref(x; a, b, c, d, So)=(x/absx)S(absx; a, b, c, d, So)$, where absx is the absolute value of variable x.

22. A computer program product comprising a computer readable medium having one or more logic instructions for
   receiving raw data in a computer, said raw data comprising data from a plurality of light detectors of a flow cytometry system; and,
   scaling said raw data using at least one scaling function that provides substantially linear transformations for data values proximal to zero and substantially logarithmic transformations for other data values to generate scaled data.

23. The computer program product of claim 22, wherein said computer readable medium comprises one or more of: a CD-ROM, a floppy disk, a tape, a flash memory device or component, a system memory device or component, a hard drive, or a data signal embodied in a carrier wave.

24. A system for analyzing flow cytometry data, comprising:
   (a) at least one flow cytometer; and,
   (b) at least one computer operably connected to said flow cytometer, said computer having system software comprising one or more logic instructions for:
      receiving raw data in said computer, said raw data comprising data from a plurality of light detectors of a flow cytometry system; and
      scaling said raw data using at least one scaling function that provides substantially linear transformations for data values proximal to zero and substantially logarithmic transformations for other data values to generate scaled data.

25. The system of claim 24, wherein said system software further comprises one or more logic instructions for displaying said scaled data for a human viewer.

26. The system of claim 24, wherein said system software further comprises one or more logic instructions for analyzing said scaled data to identify portions of said raw data of interest.

* * * * *